(12) United States Patent
Alon Cohen et al.

(10) Patent No.: US 10,987,073 B2
(45) Date of Patent: Apr. 27, 2021

(54) MEDICAL IMAGING SYSTEM AND METHOD FOR AUTOMATED MEDICAL IMAGING ASSISTANCE

(71) Applicant: General Electric Company, Schenectady, NY (US)

(72) Inventors: Talia Alon Cohen, Haifa (IL); Ken Efrati, Kiryat Motzkin (IL)

(73) Assignee: General Electric Company, Schenectady, NY (US)

( * ) Notice: Subject to any disclaimer, the term of this patent is extended or adjusted under 35 U.S.C. 154(b) by 280 days.

(21) Appl. No.: 16/220,745

(22) Filed: Dec. 14, 2018

(65) Prior Publication Data

US 2020/0187887 A1 Jun. 18, 2020

(51) Int. Cl.
*A61B 6/00* (2006.01)
*A61B 6/03* (2006.01)

(52) U.S. Cl.
CPC ............ *A61B 6/4447* (2013.01); *A61B 6/032* (2013.01); *A61B 6/037* (2013.01); *A61B 6/547* (2013.01); *A61B 6/4266* (2013.01); *A61B 6/4417* (2013.01); *A61B 6/52* (2013.01); *A61B 6/545* (2013.01)

(58) Field of Classification Search
CPC ....... A61B 6/4447; A61B 6/032; A61B 6/547; A61B 6/037; A61B 6/52; A61B 6/4266; A61B 6/545; A61B 6/4417
See application file for complete search history.

(56) References Cited

U.S. PATENT DOCUMENTS

| | | | |
|---|---|---|---|
| 8,876,377 B2 | 11/2014 | Silberklang et al. | |
| 9,078,618 B2 | 7/2015 | Stern et al. | |
| 9,579,072 B1 | 2/2017 | Grobshtein et al. | |
| 9,606,247 B2 | 3/2017 | Kovalski et al. | |
| 2013/0342578 A1* | 12/2013 | Isaacs ................... | G16H 50/70 345/634 |
| 2014/0049629 A1* | 2/2014 | Siewerdsen ............ | A61B 34/20 348/77 |
| 2015/0327831 A1 | 11/2015 | Levin et al. | |
| 2017/0000448 A1 | 1/2017 | Hefetz et al. | |

* cited by examiner

*Primary Examiner* — David P Porta
*Assistant Examiner* — Meenakshi S Sahu
(74) *Attorney, Agent, or Firm* — The Small Patent Law Group LLC; Dean D. Small

(57) ABSTRACT

A medical imaging system includes a gantry, a display device, and a control circuit. The gantry includes detector arms circumferentially spaced apart along a perimeter of a bore and radially movable towards and away from a subject. The control circuit generates a subject shape outline of the subject within the bore based on obtained contour image data of the subject. The control circuit determines designated scan positions of the detector arms based on the subject shape outline. The control circuit displays the subject shape outline on the display device within a gantry visualization that is a graphical representation of the gantry showing the bore. The control circuit displays a set of graphical detector arms on the display screen within the gantry visualization. The graphical detector arms are displayed at the designated scan positions relative to the gantry of the gantry visualization to show a subject-gantry geometric relationship.

20 Claims, 11 Drawing Sheets

MEDICAL IMAGING SYSTEM AND METHOD FOR AUTOMATED MEDICAL IMAGING ASSISTANCE

FIELD

The subject matter disclosed herein relates generally to medical imaging systems, and more particularly to providing automated assistance to an operator or technician during a medical imaging procedure.

BACKGROUND

Medical imaging systems are used to assist with diagnosis of medical ailments in patients by generating image data showing internal elements of the patients, such as organs, bones, blood, and the like. Some medical imaging systems are nuclear medicine (NM) imaging systems, which involves the application of radioactive substances (e.g., tracers) into the patient. Single Photon Emission Computed Tomography (SPECT) and Positron Emission Tomography (PET) are examples of nuclear imaging systems. A goal of nuclear medicine imaging systems is to provide high quality images of a patient to physician for analysis, while limiting the radiation exposure of an operator (e.g., an imaging technician) that administers the imaging scan.

One way to achieve high quality images of a patient is to position detection heads of the NM imaging system close to the patient during an imaging scan or procedure. However, it may be difficult for an operator for configure the positions of the detection heads relative to the patient during a set-up stage due to a relatively large number of the detection heads and/or limited accessibility to the detection heads. For example, it may be difficult for the operator to view the positions of the detection heads relative to the patient. Furthermore, once the image acquisition stage begins the detectors may rotate about the patient. Thus, even if the operator is able to see and manually set the positions of the detection heads relative to the patient at the fixed position prior to the image acquisition, the operator may not be able to manually set up the detector positioning at each rotational position. As a result, the operator may configure the detection heads in sub-optimal positions, which degrades the quality of images that can be generated during the imaging procedure relative to providing better positioning of the detection heads.

Another concern that could negatively affect the image quality is movement of the patient or other objects, such as a linen or implanted medical device, after the set-up stage. For example, if the patient moves his or her arm into one of the detection heads, the detection head may be configured to automatically retract, which increases the distance from the detection head to a target region of interest of the patient, such as the heart. The increased distance reduces the image quality. If the movement occurs during the imaging scan, the operator may be in a different room to avoid exposure to radiation, and may not be aware of the movement. Even if the operator is notified via an alarm, for example, of the contact involving one or more of the detection heads, the operator may be provided limited, if any, information that could be useful for repositioning the patient.

BRIEF DESCRIPTION

In one or more embodiments, a medical imaging system is provided that includes a gantry, a display device, and a control circuit. The gantry defines a bore configured to receive a subject therein. The gantry includes at least three detector arms circumferentially spaced apart along a perimeter of the bore and radially movable relative to the gantry towards and away from the subject. The display device includes a display screen. The control circuit includes one or more processors communicatively connected to the display device. The control circuit is configured to generate a subject shape outline of the subject disposed at least partially within the bore based on obtained contour image data of the subject. The control circuit is configured to determine designated scan positions of the detector arms based on the subject shape outline. Respective distal ends of the detector arms at the designated scan positions are within a designated threshold proximity of the subject shape outline without intersecting the subject shape outline. The control circuit is configured to display the subject shape outline on the display screen of the display device within a gantry visualization that is a graphical representation of the gantry showing the bore. The subject shape outline is displayed within the bore of the gantry visualization. The control circuit is configured to display a first set of graphical detector arms on the display screen within the gantry visualization. Each of the graphical detector arms in the first set is associated with a different one of the detector arms of the gantry. The graphical detector arms are displayed at the designated scan positions relative to the gantry of the gantry visualization to show a subject-gantry geometric relationship.

In one or more embodiments, a method (e.g., for automated medical imaging assistance) is provided that includes generating a subject shape outline of a subject disposed at least partially within a bore of a gantry of a medical imaging apparatus based on contour image data of the subject. The gantry includes at least three detector arms circumferentially spaced apart along a perimeter of the bore of the gantry. The detector arms are radially movable relative to the gantry towards and away from the subject. The method includes determining designated scan positions of the detector arms based on the subject shape outline. Respective distal ends of the detector arms at the designated scan positions are within a designated threshold proximity of the subject shape outline without intersecting the subject shape outline. The method includes displaying the subject shape outline on a display screen of a display device within a gantry visualization that is a graphical representation of the gantry showing the bore. The subject shape outline is displayed within the bore of the gantry visualization. The method also includes displaying a first set of graphical detector arms on the display screen within the gantry visualization. Each of the graphical detector arms in the first set is associated with a different one of the detector arms of the gantry, and the graphical detector arms are displayed at the designated scan positions relative to the gantry of the gantry visualization to show a subject-gantry geometric relationship.

In one or more embodiments, a medical imaging system is provided that includes a gantry, a display device, and a control circuit. The gantry defines a bore configured to receive a subject therein. The gantry includes multiple detector arms circumferentially spaced apart along a perimeter of the bore and radially movable relative to the gantry towards and away from the subject. The display device includes a display screen. The control circuit includes one or more processors communicatively connected to the display device. The control circuit is configured to generate a subject shape outline of the subject disposed at least partially within the bore based on obtained contour image data of the subject. The control circuit is configured to display the subject shape outline on the display screen within a gantry visualization that is a graphical representation of the gantry showing the bore. The subject shape outline is displayed within the bore of the gantry visualization. The control circuit is configured to determine designated scan positions of the detector arms based on the subject shape outline such that respective distal ends of the detector arms at the designated scan positions are within a designated threshold proximity of the subject shape outline without intersecting the subject shape outline. The control circuit is configured to display a first set of graphical detector arms on the display screen within the gantry visualization. Each of the graphical detector arms is associated with a different one of the detector arms of the gantry. The graphical detector arms in the first set are displayed at the respective designated scan positions relative to the gantry of the gantry visualization. The control circuit is also configured to determine current positions of the detector arms relative to the gantry, and to display a second set of graphical detector arms on the display screen within the gantry visualization. The graphical detector arms in the second set are displayed at the respective current positions of the detector arms relative to the gantry of the gantry visualization. Each of the graphical detector arms in the second set is superimposed on a corresponding graphical detector arm in the first set that represents the same detector arm of the gantry.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

Embodiments of the inventive subject matter described herein provide a medical imaging system that is configured to provide automated assistance to an operator or technician during the set-up and image acquisition stages of a medical imaging procedure. For example, the medical imaging system monitors a shape outline or contour of the subject (e.g., patient) to be imaged, as well as positions of multiple detector arms of the medical imaging apparatus, and displays a visualization on a display device that shows both the subject shape outline and the detector arm positions. The operator can view the visualization on the display device to view and comprehend a geometric relationship between the subject and the gantry. It is noted that the medical imaging system does not merely display data, but rather provides information to an operator that was not previously available to the operator using some known imaging systems. For example, the operator may not have been previously able to view or comprehend the subject-gantry geometric relationship due to a complexity of the imaging apparatus (e.g., number and positioning of the detector arms) and/or visual inaccessibility or obstruction. The medical imaging apparatus provides the operator with information that was not previously available to the operator, which may enable the generation of higher quality images due at least in part to closer positioning of the detector arms to the subject.

The operator can view the visualization on a display device remote from the gantry, which enables the operator to monitor a medical imaging procedure while the operator is out of the room to avoid radiation exposure. In addition, the medical imaging system may update the visualization in real-time to show any detected changes in the subject shape outline and/or detector arm positioning. The medical imaging system described herein allows the operator to track the progress and activity of the medical imaging procedure from a separate room, while retaining an ability to intervene in the medical imaging procedure via the use of a user input device to make adjustments, communicate with the subject, or the like. For example, if the subject deviates from an original position during the image acquisition stage, the medical imaging system may notify the operator, and the operator may physically or communicatively reposition the subject or may reposition the detector arms to achieve a desired proximity between the detector arms and the subject to enable high quality image generation.

Figure 1:
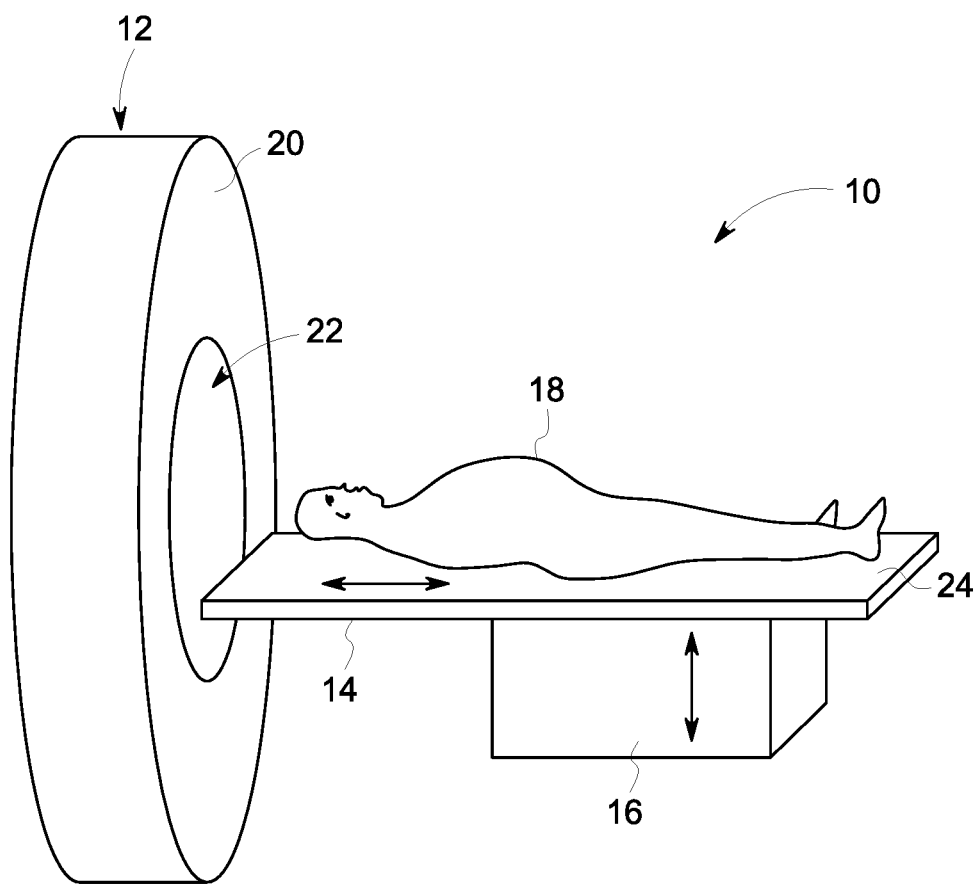
FIG. 1 shows a medical imaging system in accordance with an embodiment.

FIG. 1 shows a medical imaging system 10 in accordance with an embodiment. The medical imaging system 10 includes a medical imaging apparatus 12 and a bed 14. The medical imaging apparatus 12 includes a gantry 20 that defines a bore 22. The bed 14 includes a platform 24 that supports a subject 18, which is a human patient in the illustrated embodiment but is not limited to a human patient. For example, the subject 18 may be another living animal or an inanimate object in an alternative embodiment. The bed 14 is able to move the platform 24 longitudinally into the bore 22 for locating the subject 18 in a designated imaging position. The bed 14 includes a lift mechanism 16 that vertically raises and lowers a platform 24 for vertically positioning the subject 18 relative to the gantry 20. The medical imaging apparatus 12 includes imaging components and devices mounted to the gantry 20 for generating medical image data of the subject 18, such as image data depicting internal elements of the subject 18.

Figure 2:
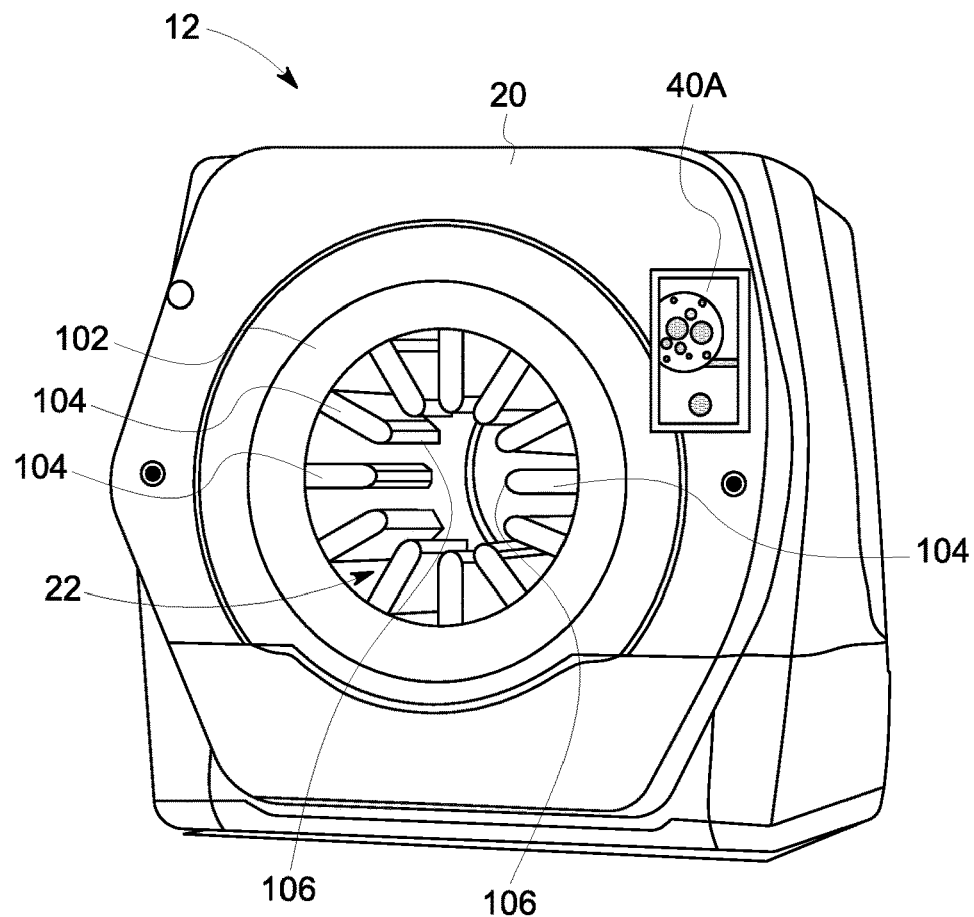
FIG. 2 is a perspective view of a medical imaging apparatus of the medical imaging system according to an embodiment.

FIG. 2 is a perspective view of the medical imaging apparatus 12 of the medical imaging system 10 (shown in FIG. 1) according to an embodiment. The medical imaging apparatus 12 includes the gantry 20 which defines the bore 22. The bore 22 is open along a front side 102 of the gantry 20, and the subject on the bed 14 is received into the bore 22 across the front side 102. As used herein, relative or spatial terms such as "front," "rear," "top," "bottom," "upper," and "lower" are only used to identify and distinguish the referenced elements according to the illustrated orientations and do not necessarily require particular positions or orientations relative to the surrounding environment of the medical imaging system 10. The bore 22 has a circular cross-sectional perimeter shape in the illustrated embodiment, but may have a different shape such as elliptical or oval in an alternative embodiment.

The gantry 20 includes at least three detector arms 104 that are mounted along the perimeter of the bore 22. The detector arms 104 perform the medical imaging scan or procedure by detecting particles and/or radiation used to generate image data. The detector arms 104 are circumferentially spaced apart from one another along the perimeter of the bore 22. Optionally, the detector arms 104 may be uniformly arranged or distributed along the perimeter, such that the spacing between adjacent detector arms 104 is constant around the entire perimeter. The gantry 20 in the illustrated embodiment includes twelve detector arms 104, but the gantry 20 may have more or less than twelve in an alternative embodiment. In a few non-limiting examples of alternative embodiments, the gantry 20 may have three, four, five, six, eight, ten, or fourteen detector arms 104 circumferentially spaced along the perimeter of the bore 22.

In the illustrated embodiment, the medical imaging apparatus 12 is a nuclear medicine (NM) imaging apparatus, such as a SPECT system or a PET system. For example, the detector arms 104 are NM cameras configured to detect and measure radiation emitted from the subject while the subject is located at least partially within the bore 22. For example, a radioactive tracer may be administered to the subject such that the tracer is within an internal element of the subject, such as bone, organ, blood, or the like. In SPECT systems, the detector arms 104 detect and measure gamma rays that are emitted by the radioactive tracer. The detected gamma rays are used by the SPECT system to construct image data depicting the internal element of the subject. In PET systems, the radioactive tracer decays to produce positrons, and the detector arms 104 monitor photons resulting from collisions between the positrons and electrons within the subject. The medical imaging apparatus 12 may be a SPECT system, a PET system, or another type of NM system.

The detector arms 104 are radially movable (e.g., extendable) relative to the gantry 20, such that the detector arms 104 can be controlled to radially towards a center of the bore 22 and to move away from the center of the bore 22. For example, during a medical imaging scan, the detector arms 104 may be controlled to move towards and/or away from the subject disposed within the bore 22. In the illustrated embodiment, the detector arms 104 are shown in an extended position relative to the gantry 20. In the extended position, the detector arms 104 project from the gantry 20 into the bore 22. The detector arms 104 are radially movable to position the detector arms 104 proximate to the subject. In NM imaging, the image resolution and quality diminish with increasing distance of the detectors from the target region of interest within the subject, such as the heart in an example. The detector arms 104 are movable to allow the detector arms 104 to be retracted away from the subject while the subject is being loaded and unloaded relative to the bore 22, and to extend towards the subject during the imaging scan to be proximate to the subject for generating high resolution and high quality images of internal element (s) of the subject.

The detector arms 104 may include detection heads at or proximate to distal ends 106 of the detector arms 104. The detection heads represent the one or more devices used for monitoring, detecting, capturing, measuring, filtering, and guiding the particles and/or radiation (e.g., gamma rays) emitted from the subject that are processed for generating the medical image data. The detection heads may include single crystal detectors, multi-crystal detectors, pixelated detectors, and/or scintillator-based detectors that are configured to acquire NM image data, such as SPECT image data, based on radiation emitted from the subject. The detection heads may include various semiconductor materials or non-semiconductor crystal scintillator materials. The detection heads may include collimators. The detection heads may be housed within the detector arms 104 at or proximate to the distal ends 106.

The gantry 20 optionally includes a display device 40 mounted along the front side 102. The display device 40 is viewable to an operator administering the medical imaging procedure for the subject. As used herein, the operator is broadly intended to include human persons that utilize and interact with the medical imaging apparatus 12 within the scope of employment, such as technicians, technologists, doctors, nurses, technology maintenance workers, and the like.

Figure 3:
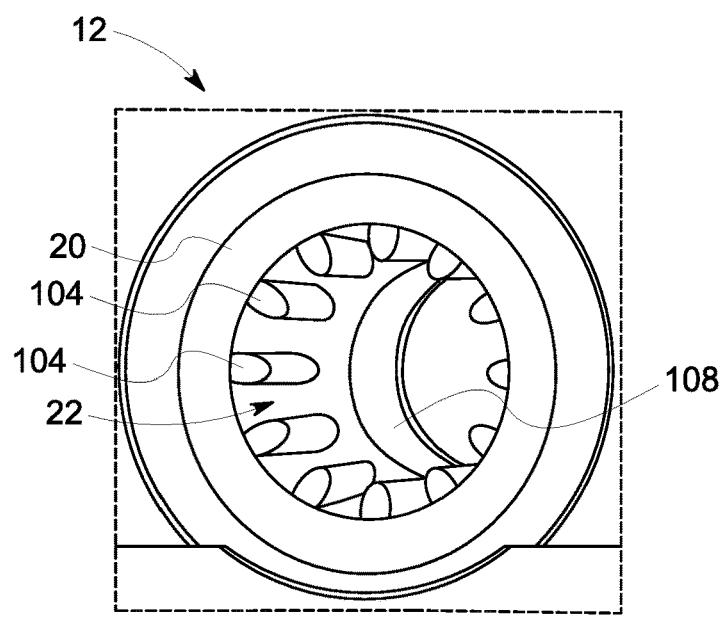
FIG. 3 is a perspective view of a portion of the medical imaging apparatus shown in FIG. 2 showing detector arms in a retracted position relative to a gantry.

FIG. 3 is a perspective view of a portion of the medical imaging apparatus 12 shown in FIG. 2 showing the detector arms 104 in a retracted position relative to the gantry 20. Compared to the extended position shown in FIG. 2, the detector arms 104 extend a shorter distance or length into the bore 22 when in the retracted position. The detector arms 104 may be independently movable such that different detector arms 104 may extend different lengths or distances into the bore 22 in order to extend close to the subject, as it is recognized that the shape or contour of the subject is typically irregular (e.g., not perfectly cylindrical).

The medical imaging apparatus 12 optionally includes an additional imaging modality device 108 as an add-on. For example, the additional imaging modality device 108 may be a computed tomography (CT) camera which is mounted to the gantry 20 rearward of the detector arms 104 along an axial length of the bore 22.

Figure 4:
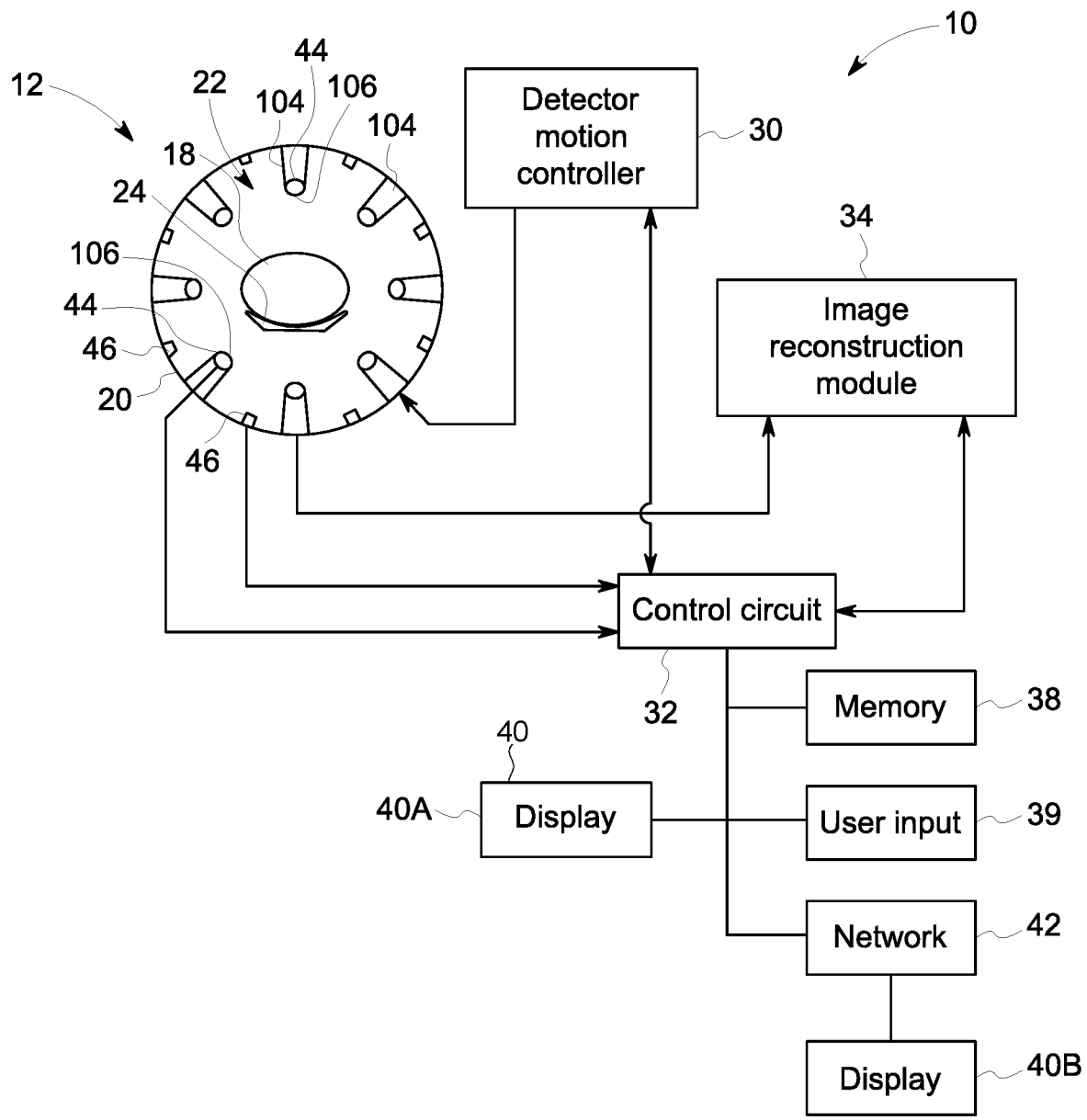
FIG. 4 is a block diagram of the medical imaging system according to an embodiment.

FIG. 4 is a block diagram of the medical imaging system 10 according to an embodiment. FIG. 4 also illustrates a front end view of the gantry 20, showing a subject 18 on the platform 24 within the bore 22. The gantry 20 in the illustrated embodiment has eight detector arms 104 circumferentially spaced along the perimeter of the bore 22, but alternatively may have twelve detector arms 104 as shown in FIGS. 2 and 3. The medical imaging system 10 includes the gantry 20, at least one display device 40, and a control circuit 32.

The control circuit 32 includes one or more processors and associated circuitry. For example, the control circuit 32 includes and/or represents one or more hardware circuits or circuitry that include, are connected with, or that both include and are connected with one or more processors, controllers, and/or other hardware logic-based devices. The control circuit 32 may include a central processing unit (CPU), one or more microprocessors, a graphics processing unit (GPU), or any other electronic component capable of processing inputted data according to specific logical instructions. The control circuit 32 may be operably connected to a memory storage device 38 (referred to herein as memory 38). The memory 38 is a tangible and non-transitory computer readable medium. The memory 38 may include or represent a flash memory, RAM, ROM, EEPROM, and/or the like. The control circuit 32 may execute programmed instructions stored on the memory 38 or stored on another tangible and non-transitory computer readable medium. For example, the control circuit 32 may be configured to generate a gantry visualization that shows a subject-gantry relationship for display on one or more of the display devices 40 by executing the programmed instructions stored on the memory 38. The memory 38 optionally may store additional information that is accessible to and utilized by the control circuit 32 as described herein, such as databases, look-up tables, mathematical equations, calibration constants, and/or the like. For example, the memory 38 may store a patient chart specific to the subject 18 and/or a patient database that contains information aggregated from historical data on patients other than the subject 18.

Optionally, the control circuit 32 and the memory 38 may be integrated components of the medical imaging apparatus 12. For example, the control circuit 32 and memory 38 may be parts of an onboard computing device mechanically housed in or on the gantry 20. The onboard computing device may include the display 40A (also shown in FIG. 2). The control circuit 32 is communicatively connected to the at least one display device 40 via wired or wireless communication links. In the illustrated embodiment, the medical imaging system 10 includes a first display device 40A that is mounted on the gantry 20, as shown in FIG. 2, and a second display device 40B that is separate (e.g., remote) from the gantry 20. The second display device 40B may be located in a different room than the gantry 20. For example, the second display device 40B may be located in an office of the operator that is separate from the imaging room that houses the medical imaging apparatus 12. The control circuit 32 may be conductively connected to the first display device 40A via a wire or cable. The control circuit 32 may be connected to the second display device 40B via a network 42. The network 42 may be a wireless network, such that the control circuit 32 generates wireless signals that are transmitted or broadcast to the second display device 40B. Alternatively, the network 42 may be a wired network, such as an Ethernet or Local Area Network (LAN), that connects the control circuit 32 to the second display device 40B.

Alternatively, the control circuit 32 and the memory 38 may be discrete and separate from the medical imaging apparatus 12 (e.g., gantry 20). For example, the control circuit 32 and the memory 38 may be components of a remote computing device, such as a handheld tablet, smartphone, or workstation of the operator (e.g., medical technician, nurse, doctor, or the like). The remote computing device may communicate with one or more components of the medical imaging apparatus 12 via wired cables and/or wireless links.

The medical imaging system 10 also includes a detector motion controller 30 that controls the movement of the detector arms 104 relative to the gantry 20, and also controls the operation of the detection heads within the detector arms 104. The detector motion controller 30 includes one or more processors that operate according to programmed instructions stored on a memory device. For example, the detector motion controller 30 may individually control the radial extension of each of the detector arms 104 between the retracted and extended positions. The detector motion controller 30 may also rotate or orbit the detector arms 104 around the subject 18 as a collective unit. In an embodiment, the detector motion controller 30 may control the detection heads to rotate, pivot, or swivel about respective axes that are substantially parallel to the longitudinal (or depth) axis of the bore 22, and this swiveling allows each of the detection heads to scan the subject 18 with a fan-shaped field of view. The swiveling of the detection heads may be relative to the detector arms 104, such that the detector arms 104 may be stationary while the detection heads swivel within the detector arms 104.

The detector motion controller 30 may be communicatively connected to the control circuit 32. For example, as described herein, the control circuit 32 may generate a control signal that provides the detector motion controller 30 with designated scan positions of the detector arms 104 for an upcoming medical imaging scan of the subject 18. In response to receiving the control signal, the detector motion controller 30 may extend the detector arms 104 relative to the gantry 20 to position the detector arms 104 in the designated scan positions. In another example, the detector motion controller 30 may periodically, or on command, generate a status signal for the control circuit 32 that identifies the current positions of each of the detector arms 104, such as the current extension positions, relative to the gantry 20. Upon receiving the status signal, the control circuit 32 may display graphical detector arms in a gantry visualization on one or more of the display devices 40A, 40B such that the graphical detector arms are displayed in equivalent positions relative to the gantry visualization as the actual detector arms 104 are currently positioned relative to the actual gantry 20.

The medical imaging system 10 also includes an image reconstruction module 34 that is configured to generate medical images from image data generated by the detector arms 104 (and detection heads thereof). The image data from the detector arms 104 may include projection data, positioning data, detected energy data, and/or the like. The image reconstruction module 34 may include one or more processors that operate according to programmed instructions to use NM image reconstruction techniques to generate NM images, such as SPECT images, of the subject 18. The image reconstruction module 34 is communicatively connected to the detector arms 104 to receive the image data. The image reconstruction module 34 may receive the data directly from the detector arms 104, indirectly via the control circuit 32, or indirectly from an acquisition console. The image reconstruction module 34 in an embodiment is connected directly to the gantry 20, such as residing within a common hardware device (e.g., housing) or software module as the control circuit 32. In an alternative embodiment, the image reconstruction module 34 may be remote from the gantry 20, such as residing on a remote server (e.g., in the cloud) and connected to the control circuit 32 via the network 42.

The NM images depict internal elements within the subject 18, and may include a target element or region of interest such as the heart or another organ. The NM images may be three-dimensional or two-dimensional. The NM images may be stored in the memory 38 or another storage medium. The control circuit 32 may access the NM images to display the NM images on one or more of the display devices 40A, 40B, and/or to communicate the NM images remotely via the network 42.

The medical imaging system 10 also includes a user input device 39 that enables an operator to intervene and participate in both the set-up and scan of the medical imaging procedure, as described herein. The user input device 39 may include a touchpad, touchscreen, keyboard, computer mouse, trackball, physical buttons and/or dials, and/or the like. The operator can use the user input device 39 to make user input selections, which are communicated as signals to the control circuit 32. The user input device 39 optionally may be integrated into a common hardware device as one of the display devices 40A, 40B. Optionally, each of the display devices 40A, 40B may be incorporated with a different user input device 39, which allows the operator to communicate and intervene in the medical imaging procedure from either of the locations of the display devices 40A, 40B, such as in the imaging examination room at the first display device 40A or in the separate operator office at the second display device 40B.

In the illustrated embodiment, the medical imaging apparatus 12 of the medical imaging system 10 includes engagement sensors 44 mounted at the distal ends 106 of the detector arms 104. The engagement sensors 44 are configured to detect physical contact between the detector arms 104 and the subject 18 and any objects associated with the subject 18 within the bore 22, such as linens, the platform 24 of the bed 14 (shown in FIG. 1), and the like. The engagement sensors 44 may be (or include) mechanical switches, such as pressure sensors and other force sensors, and alternatively may be or include proximity sensors, capacitive sensors, or the like. Physical engagement between the detector arms 104 and the subject 18 may degrade the image quality of the NM images, so the engagement sensors 44 are used to ensure that the detector arms 104, although proximate to the subject 18, remain spaced apart from the subject 18 during the medical imaging scan to provide high quality NM images.

The medical imaging apparatus 12 also includes contour sensors 46 in the illustrated embodiment. The contour sensors 46 are mounted to the gantry 20 along the perimeter of the bore 22. The contour sensors 46 optionally may be disposed in the gaps between the detector arms 104, as shown in FIG. 4. The contour sensors 46 are utilized during a contour scan of the subject 18 to provide contour image data. The contour image data generated by the contour sensors 46 is processed by the control circuit 32 to generate a subject shape outline of the subject 18. The subject shape outline is utilized during the medical imaging set-up to determine the designated scan positions of the detector arms 104 for the medical imaging scan. The control circuit 32 also displays the subject shape outline on one or more of the display devices 40A, 40B within the gantry visualization to enable the operator to view and comprehend the subject-gantry geometric relationship. The contour sensors 46 may be any of various types of sensors, such as optical imaging sensors, ultrasound sensors, or the like. The contour sensors 46 and the engagement sensors 44 are communicatively connected to the control circuit 32 to provide the respective sensor data to the control circuit 32.

Figure 5:
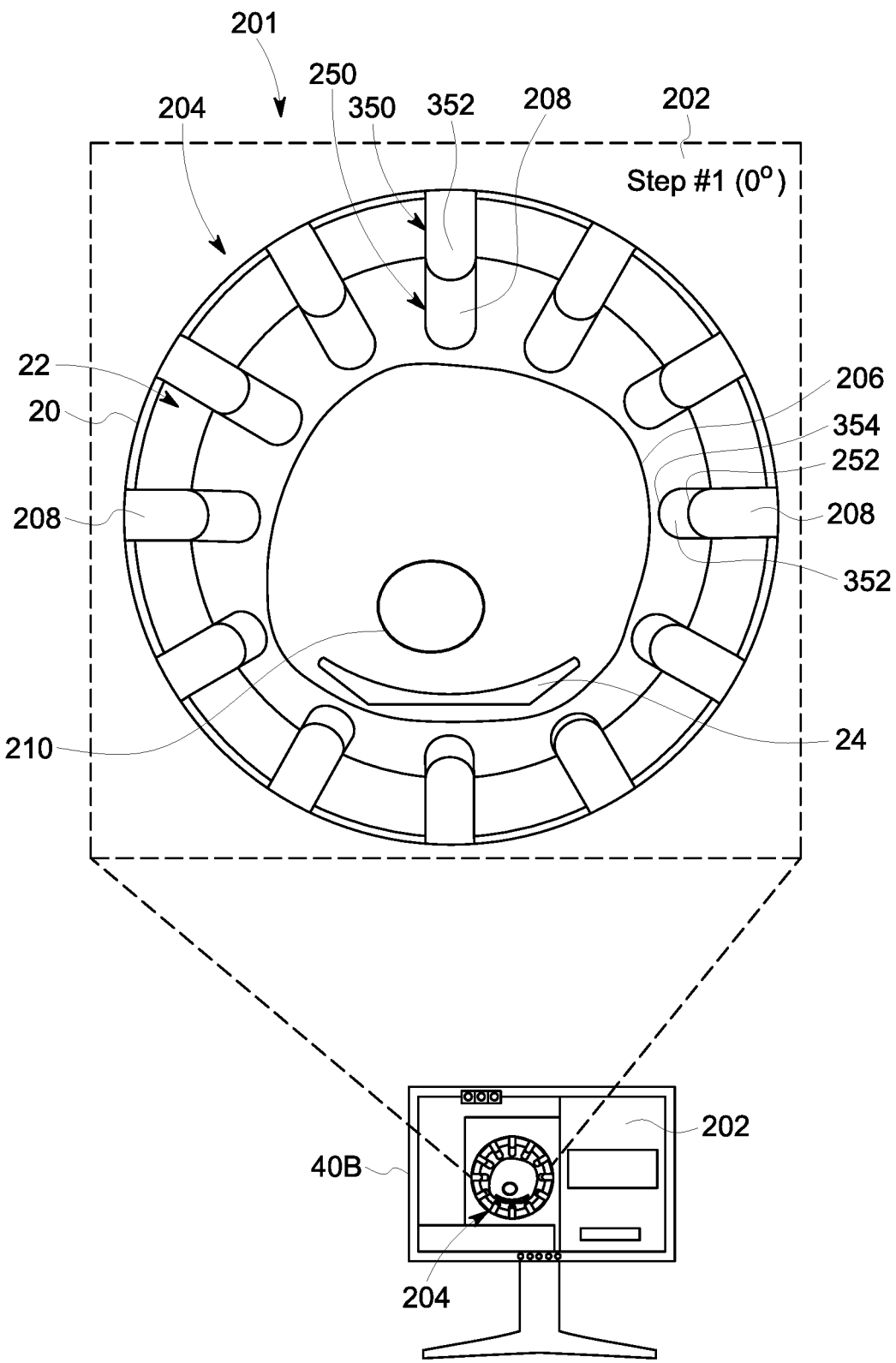
FIG. 5 illustrates a display device of the medical imaging system and an enlarged inset view showing a portion of a display screen of the display device displaying a gantry visualization according to an embodiment.

FIG. 5 illustrates the second display device 40B of the medical imaging system 10 and an enlarged inset view 201 showing a portion of a display screen 202 of the second display device 40B displaying a gantry visualization 204 according to an embodiment. The display device 40B in the illustrated embodiment includes or represents a monitor that may be connected to a desktop computer or a laptop computer. In a non-limiting example, the display device 40B may be located in a separate room than the gantry 20 (shown in FIG. 2), such as in an operator office near an imaging room that houses the gantry 20. In another embodiment, the display device 40B may be a handheld computing device, such as a tablet computer, a smartphone, or the like. The display screen 202 is configured to be viewable to an operator.

The control circuit 32 (shown in FIG. 4) of the medical imaging system 10 (FIG. 4) is configured to generate the gantry visualization 204 that is displayed on the display screen 202. The gantry visualization 204 is a graphical representation of a portion of the medical imaging apparatus 12 (shown in FIG. 2) including the gantry 20 and the bore 22. The gantry visualization 204 is designed to resemble the medical imaging apparatus 12, such that the operator can visualize and understand up-to-date parameters, positioning, and/or operation of the medical imaging apparatus 12 by viewing the display device 40B without viewing the actual medical imaging apparatus 12.

Optionally, the gantry visualization 204 may be part of a graphical user interface, which enables an operator using the user input device 39 (shown in FIG. 4) to interact with and modify the gantry visualization 204 by selecting various items displayed on the gantry visualization 204. Alternatively, the gantry visualization 204 may be non-interactive, and the operator may interact with a separate user interface discrete from the gantry visualization 204 to modify the appearance of the gantry visualization 204.

The gantry visualization 204 shows an end view of the gantry 20 oriented along the longitudinal (or depth) axis of the bore 22. The end view may be a cross-sectional view that shows some components in cross-section. In addition to showing graphical representations of the gantry 20 and the bore 22, the gantry visualization 204 also shows graphical detector arms 208 that graphically represent the detector arms 104. The gantry visualization 204 also includes a subject shape outline 206 of the subject that is disposed, at least partially, within the bore 22 of the gantry 20 for the medical imaging scan. Optionally, the gantry visualization 204 also shows a graphical representation of the platform 24 supporting the subject, as well as a target region indicator 210 that represents a target region of interest of the subject. The target region of interest may be an area of the subject to which the detector arms 104 are focused during medical imaging scan. The target region of interest may include an organ, such as the heart.

The graphical detector arms 208 correspond to the detector arms 104, such that there are twelve graphical detector arms 208 to match the twelve detector arms 104 shown in FIGS. 2 and 3. The graphical detector arms 208 are displayed on the gantry visualization 204 at equivalent or analogous locations along the perimeter of the bore 22 as the corresponding actual (e.g., physical) detector arms 104. The graphical detector arms 208 are radially elongated to extend at least partially into the virtual bore 22. The subject shape outline 206 is displayed on the gantry visualization 204 within the bore 22. The target region indicator 210 is displayed within the subject shape outline 206. The locations of the displayed components relative to the gantry 20 in the gantry visualization 204 are based on the known, measured, estimated, and/or computed locations of the respective components relative to the actual gantry 20. Therefore, the operator can view the gantry visualization 204 to perceive the subject-gantry geometric relationship, such as by viewing the relative positioning of the graphical detector arms 208 to the subject shape outline 206.

One immediately recognizable technical effect of the displayed gantry visualization 204 is that the operator can view the subject-gantry geometric relationship without being in a line-of-sight of the bore 22. For example, the operator may even be located in a separate room as the gantry 20 while viewing the gantry visualization 204, which beneficially reduces the operator's exposure to radiation relative to the operator being within the same room as the gantry 20 and peering into the bore 22 to view the positions of the detector arms 104 relative to the subject. Another technical effect of the displayed gantry visualization 204 that may not be as immediately recognizable is that the operator may not be able to view and interpret the subject-gantry geometric relationship in the physical medical imaging apparatus 12. For example, the end view shown in the gantry visualization 204 may not be perceivable to an operator by peering into the bore 22 of the gantry 20. The twelve circumferentially-arranged detector arms 104 may be difficult, if not impossible, for the operator to view based on the number and arrangement of the detector arms 104, and various other components, such as the bed 14 and a housing of the gantry 20 may obstruct the operator's visual access.

Furthermore, even if it is possible for the operator to view all of the detector arms 104 of the gantry 20 in the orientation shown by the gantry visualization 204, such as by acquiring one or more images of the detector arms 104 using a camera, another technical effect of the medical imaging system 10 described herein is that the gantry visualization 204 provides information that is not attainable merely by sight or imaging alone. For example, as described herein in more detail, the subject shape outline 206 displayed in the gantry visualization 204 is generated by aggregating specific subsets of transaxial contour slices depicting the subject in the bore 22. The subject shape outline 206 therefore may have a different shape than the shape of an outline of the subject as seen by a person or camera looking into the bore 22. Furthermore, the gantry visualization 204 may show the graphical detector arms 208 in prospective positions and current positions, whereas a person or camera looking into the bore 22 would only be able to capture the current positions of the detector arms 104. The gantry visualization 204 described herein may integrate various imaging modalities and technology to provide information to the operator about the medical imaging system 10 that may not have been available to the operator using known medical imaging systems and display technology. The medical imaging system 10 provides automated assistance to the operator for the medical imaging procedure, including during the set-up and scanning stages. Additional features and benefits of the medical imaging system 10 are described below.

Figure 6:
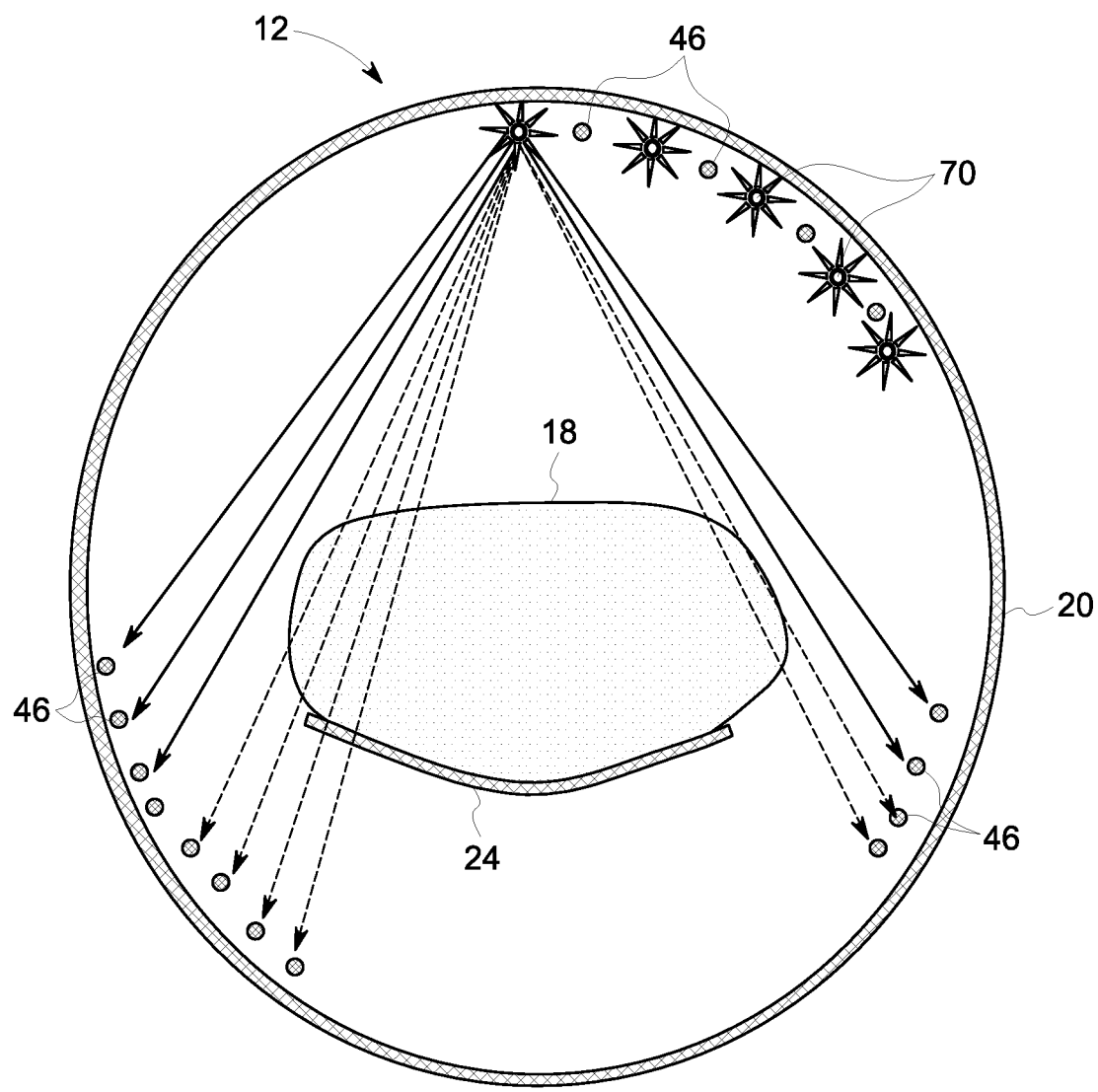
FIG. 6 illustrates the medical imaging apparatus of the medical imaging system during a contour scan according to an embodiment.

FIG. 6 illustrates the medical imaging apparatus 12 of the medical imaging system 10 during a contour scan according to an embodiment. The contour scan is performed to generated contour image data, which is used to generate the subject shape outline 206 (shown in FIG. 5). The contour scan estimates the shape of the subject 18 within the bore 22. The contour scan is performed prior to the medical imaging scan that utilizes the detector arms 104 (shown in FIG. 2) to generate medical image data, such as data for constructing SPECT images. The contour scan may be performed periodically throughout the medical imaging procedure, such as during set-up and subject positioning and also during the medical imaging scan, in order to provide a subject shape outline 206 that is updated in real-time.

In the illustrated embodiment, the gantry 20 includes the contour sensors 46 and light emitting sources 70 installed along a perimeter of the bore 22. The contour sensors 46 in the illustrated embodiment may be light detectors, such as photo-diodes. The light emitting sources 70 may be light emitting diodes (LEDs) or the like. The contour sensors 46 and the light emitting sources 70 may be installed in at least one ring around the perimeter of the bore 22 such that the contour sensors 46 are evenly spaced around the perimeter, although FIG. 6 may show less than an entirety of the contour sensors 46 and the light emitting sources 70 that represent a single ring. The gantry 20 may have multiple rings of the contour sensors 46 and light emitting sources 70 at different depths along the bore 22.

Optionally, the light emitting sources 70 may be controlled to emit light at different times according to an ordered sequence. The light emitted from any particular light emitting source 70 only arrives at some of the contour sensors 46 based on the light emission angle and the shape of the subject 18. As shown in FIG. 6, the solid lines indicate that emitted light rays or beams has impinged upon a contour sensor 46, and the dashed lines indicate that emitted light rays have not impinged upon a contour sensor 46 because such light rays were absorbed, reflected, or otherwise obscured by the subject 18. At a particular time, the control circuit 32 (or other control device performing the contour scan) knows which light emitting source 70 emitted a particular light and receives contour image data indicating which contour sensors 46 received (e.g., detected) that particular light. The control circuit 32 can estimate the shape or contour of the subject 18 using the contour image data across multiple time instances.

In an embodiment, the contour scan may include generating a collection of transaxial contour slices 212 (shown in FIG. 7) of the subject 18. For example, each sequence of light pulses from the light emitting sources 70 may result in a set of contour image data generated by the contour sensors 46. Each set of contour image data may be processed to generate a single transaxial contour slice that represents the contour of the subject 18 at one axial position along the length of the subject 18. In an embodiment, the contour scan may generate the collection of transaxial contour slices by moving the subject 18 at different axial positions within the bore 22. For example, the bed 14 (shown in FIG. 1) may be controlled to move the platform 24 in the axial direction during the contour scan (e.g., while the light emitting sources 70 emit light pulses and the contour sensors 46 detect the light) to generate a multitude of transaxial contour slices of the subject 18 at different axial positions along the length of the subject 18.

In an alternative embodiment, the contour sensors 46 may be range finders installed along the perimeter of the bore 22 instead of using the light emitting sources 70 and the light detectors. For example, the contour sensors 46 may be ultrasonic transducers that emit short pulses of sound and interpret the timing of sound wave echoes to determine the distance to the subject 18. In another example, the contour sensors 46 may be optical transducers, such as laser rangefinders that emit short pulses of light and interpret the timing of reflected light to determine the distance to the subject 18. In yet another alternative embodiment, instead of having the contour sensors 46, the detector arms 104 may generate the contour image data without additional hardware based on detecting scatter radiation during preliminary imaging of the subject 18. The scatter radiation is at energy levels below the original energy peak of the radioactive isotope administered into the subject 18. In another alternative embodiment, the medical imaging apparatus 12 may include a 3D optical camera that generates the contour image data using, for example, infrared light.

Figure 7:
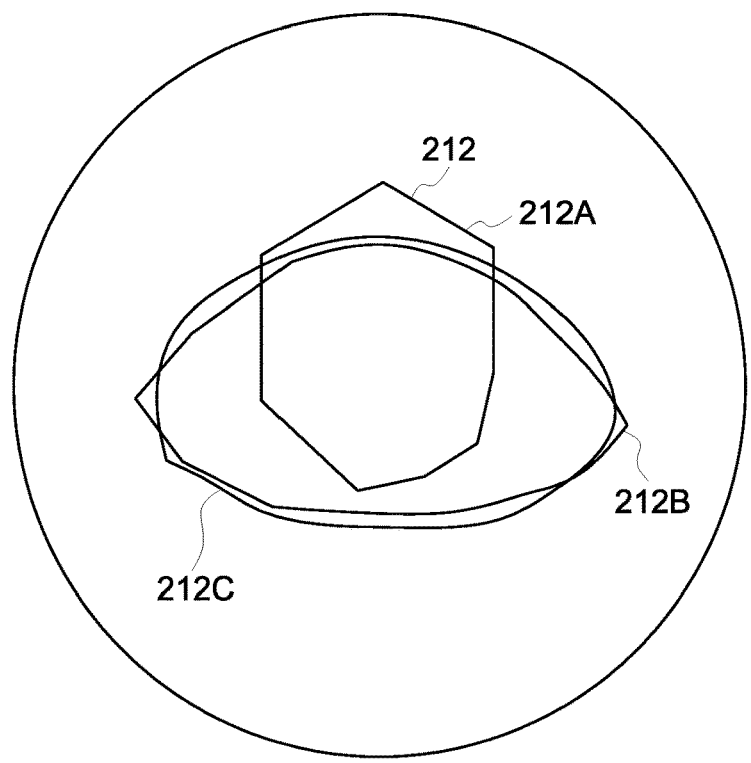
FIG. 7 illustrates a set of three transaxial contour slices depicting different axial portions of a subject according to an embodiment.

FIG. 7 illustrates a set of three transaxial contour slices 212 depicting different axial portions of the subject according to an embodiment. The transaxial contour slices 212 may be generated based on contour image data as described above. For example, a first transaxial contour slice 212A may represent the contour or outline of a first axial portion of the subject, a second transaxial contour slice 212B may depict the outline of a second axial portion of the subject, and a third transaxial contour slice 212C may depict the outline of a third axial portion of the subject. The first transaxial contour slice 212A has a taller, narrower outline than the second and third contour slices 212B, 212C. For example, the first transaxial contour slice 212A may depict the outline of the feet or the head of the subject. The second and third contour slices 212B, 212C are broader than the first contour slice 212A, and may represent the chest or torso of the subject. As the contour image data may be generated at different times, the subject's chest at the same and/or proximate axial positions may have different outlines based at least in part on the differences in volume of air within the lungs as the subject breathes.

Figure 8:
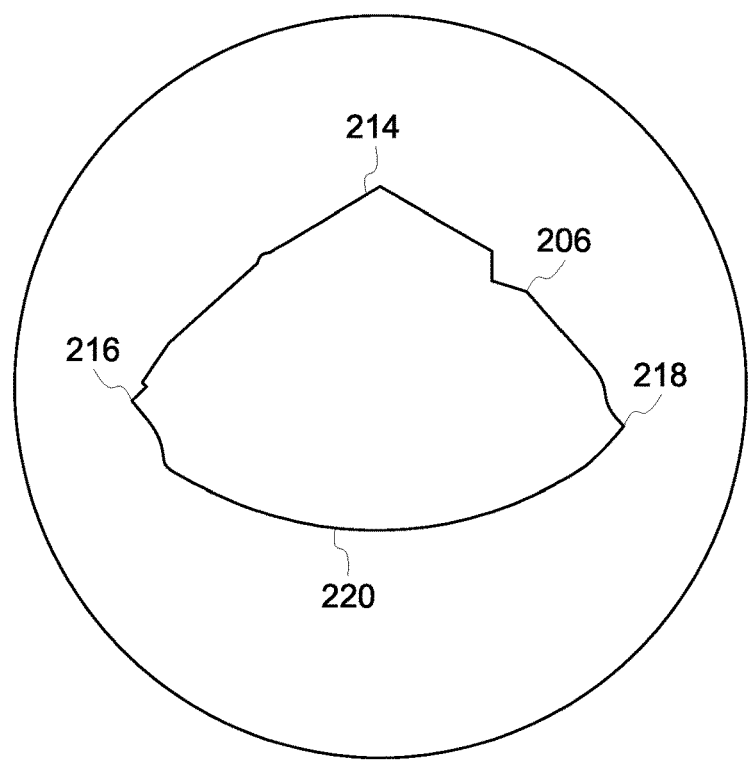
FIG. 8 illustrates a subject shape outline that is generated based on the set of transaxial contour slices shown in FIG. 7.

FIG. 8 illustrates a subject shape outline 206 that is generated based on the set of transaxial contour slices 212 shown in FIG. 7. In an embodiment, the subject shape outline 206 is generated by aggregating the transaxial contour slices 212 and selecting the maximum extent of the aggregated outline of the transaxial contour slices 212. For example, the subject shape outline 206 is a union of the most expansive parts of the perimeters of the individual contour slices 212A-C when the contour slices 212A-C are overlaid on one another as shown in FIG. 7. When the contour slices 212A-C are overlaid on one another and aligned relative to a common reference point, the outer perimeter of the resulting shape represents the subject shape outline 206. For example, a top section 214 of the subject shape outline 206 takes its shape from the first transaxial contour slice 212A, a left section 216 and a right section 218 take their shape from the second transaxial contour slice 212B, and a bottom section 220 takes its shape from the third transaxial contour slice 212C.

With additional reference back to FIG. 4, the subject shape outline 206 may be utilized by the control circuit 32 for positioning the detector arms 104 during the upcoming medical imaging scan. For example, the control circuit 32 may determine designated scan positions of the detector arms 104, which represent the extension positions of the detector arms 104 for generating the medical image data (e.g., the positions of the detector arms 104 to receive the gamma rays emitted from the subject 18). The designated scan positions are selected such that when the detector arms 104 are at the designated scan positions, the distal ends 106 of the detector arms 104 are within a designated threshold proximity of the subject shape outline 206 without intersecting the subject shape outline 206. The designated threshold proximity may be a distance that is selected to ensure a satisfactory level of medical image quality or definition. In non-limiting examples, the designated threshold proximity may be a distance of 8 cm, 5 cm, 3 cm, 1 cm, or the like. The detector arms 104 are moved from retracted positions to the designated scan positions after the subject 18 is loaded into the bore 22 to perform the medical imaging scan. For example, the detector arms 104 may move towards the subject 18 until each of the detector arms 104 is within the designated threshold proximity of the subject shape outline 206, such as within 3 cm of the outline 206.

It is recognized that the subject shape outline 206 is an amalgamation of multiple transaxial contour slices 212 and does not depict an actual portion of the subject 18. Therefore, the designated scan positions of the detector arms 104 may be determined by first mapping the subject shape outline 206 to the gantry 20 to determine the positioning of the subject shape outline 206 relative to the gantry 20. The subject shape outline 206 may be mapped to the gantry 20 based at least in part on the known locations of the contour sensors 46 relative to the gantry 20 and the measured proximity of the subject 18 to the contour sensors 46 during the contour scan. Once the subject shape outline 206 is mapped to the gantry 20, each point along the subject shape outline 206 may be classified by coordinates within a physical coordinate system of the gantry 20. The locations of the detector arms 104 relative to the gantry 20 (e.g., the circumferential locations of the arms 104) are also known, and optionally may be classified by coordinates in the same physical coordinate system. Based on the locations of the detector arms 104 and the subject shape outline 206, the control circuit 32 can determine designated scan positions for each of the detector arms 104. For example, the control circuit 32 may determine that the designated scan position for a given detector arm 104 of the gantry 20 is at a first pair of two-dimensional coordinates, and may determine that the designated scan position for another given detector arm 104 is at a second pair of two-dimensional coordinates.

Referring now back to FIG. 5, once the subject shape outline 206 is generated, the control circuit 32 is configured to display the subject shape outline 206 on the gantry visualization 204 within the graphical representation of the bore 22. The control circuit 32 may be configured to generate a transfer function in order to display the subject shape outline 206 in a location, size, and orientation within the bore 22 of the gantry visualization 204 that is analogous or equivalent to the would-be location, size, and orientation of the subject shape outline 206 within the physical bore 22. As described above, the subject shape outline 206 may be mapped to the physical dimensions and coordinates of the gantry 20. The gantry visualization 204 may be a scale representation of the gantry 20. Using one or more reference points and the known physical coordinates of the subject shape outline 206 relative to the gantry 20, a transfer function may be generated that converts the physical coordinates to virtual coordinates within the gantry visualization 204. The control circuit 32 may display the subject shape outline 206 on the gantry visualization 204 by using the transfer function to ensure that the shape, size, location, and orientation of the subject shape outline 206 relative to the gantry visualization 204 correspond accurately with the physical coordinates.

The gantry visualization 204 is tool designed to assist the operator during both the set-up and the scanning stages of the medical imaging procedure. For example, several functions of the gantry visualization 204 during set-up are described below.

In one or more embodiments, once the designated scan positions of the detector arms 104 are determined, the control circuit 32 displays a first set 250 of the graphical detector arms 208 on the gantry visualization 204. Each of the graphical detector arms 208 in the first set 250 is associated with a different one of the actual detector arms 104 of the gantry 20, and is displayed in an analogous location along the virtual gantry 20 to the physical location of the associated detector arm 104 relative to the gantry 20. The graphical detector arms 208 in the first set 250 are displayed at the designated scan positions for the associated detector arms 104. For example, distal ends 252 of the graphical detector arms 208 in the first set 250 are shown on the gantry visualization 204 proximate to the subject shape outline 206, without intersecting the subject shape outline 206. The control circuit 32 displays the graphical detector arms 208 at the designated scan positions during the set-up stage, while the actual detector arms 104 are at retracted positions.

The display of the graphical detector arms 208 at the designated scan positions assists the operator with pre-scan detector positioning and/or patient positioning with the goal of enhanced image quality due to closer proximity of the detector arms 104 to the subject (e.g., the target region of the subject). By viewing the gantry visualization 204 on the display screen 202, the operator can see the proximity of each graphical detector arm 208 at the respective designated scan position to the subject shape outline 206 even before the detector arms 208 are moved to the designated scan positions. The ability to view prospective positioning of the detector arms 104 prior to moving the detector arms 104 may provide the operator with confidence that the detector arms 104 will not contact the subject as the detector arms 104 move towards the subject during the scanning stage. Based on the information provided by the gantry visualization 204, the operator may utilize the user input device 39 (shown in FIG. 4) to manipulate one or more of the designated scan positions of the detector arms 104, to reposition the subject, and/or to adjust the axial positioning of the subject relative to the detector arms 104 (along the longitudinal or depth axis).

In an embodiment, the medical imaging system 10 allows the operator to axially scroll along the length of the subject to view different versions of the subject shape outline 206 on the gantry visualization 204 representing different positions along the length of the subject. By viewing the different versions of the subject shape outline 206, the operator can determine whether or not to adjust the axial positioning of the subject (along the longitudinal axis) relative to the detector arms 104.

Figure 9:
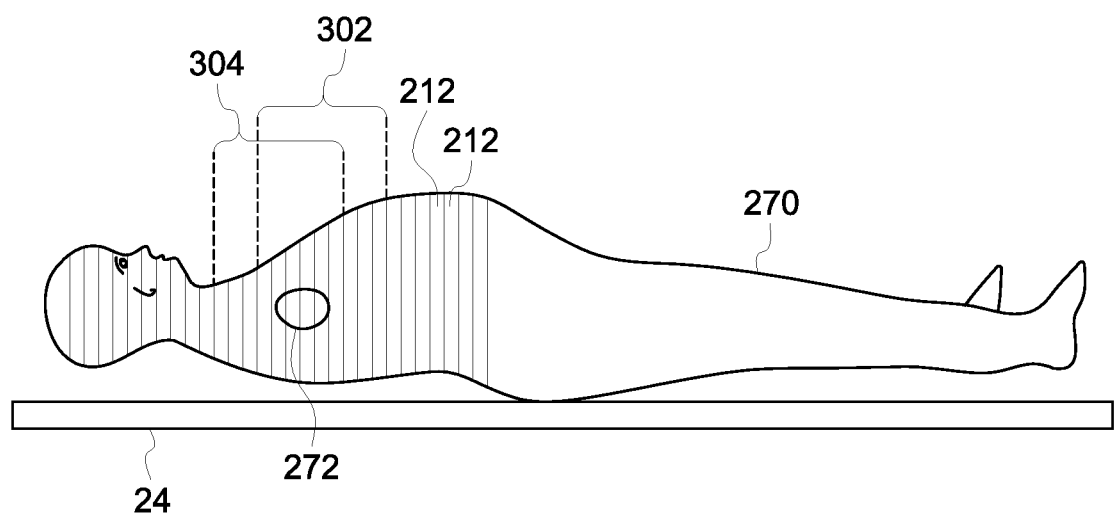
FIG. 9 is a diagram showing a side view of a human patient that represents the subject lying on a platform according to an embodiment.

FIG. 9 is a diagram showing a side view of a human patient 270 that represents the subject lying on the platform 24 according to an embodiment. An upper portion of the patient is segmented by a plurality of the transaxial contour slices 212 generated during the contour scan of the patient. In an embodiment, the subject shape outline 206 is generated based on a subset of the transaxial contour slices 212. The subset of the transaxial contour slices 212 may correspond to a longitudinal length or depth of the detector arms 104. For example, if the detector arms 104 extend a depth of 40 cm, the subject shape outline 206 may be generated based on a subset of the transaxial contour slices 212 that span at least 40 cm along the length of the patient 270. Assuming uniform slice thickness and spacing between slices 212, the subset may be represented by a given number of consecutive transaxial contour slices 212 along the length, such as 10, 20, 50, or 100 slices 212. In a non-limiting example, each slice 212 has a thickness of about 0.5 cm, so a subset of 80 consecutive, non-overlapping slices 212 spans an axial length of 40 cm along the patient 270. FIG. 9 shows a first subset 302 of transaxial contour slices 212 and a second subset 304 of transaxial contour slices 212. The first subset 302 spans a first axial segment of the patient 270, and the second subset 304 spans a second axial segment of the patient 270. The first axial segment overlaps the second axial segment, but in general the first axial segment of the patient depicts the patient's middle torso and the second axial segment depicts the patient's upper torso. The first and second subsets 302, 304 may have equal axial lengths and/or may have the same number of slices 212. In a non-limiting example, each of the first and second subsets 302, 304 may be comprised of 80 consecutive slices 212, although some of the slices 212 in an overlapping region are part of both the first and second subsets 302, 304.

In the illustrated embodiment, the medical imaging procedure is performed to generate image data of a target region of interest 272 of the patient 270. The target region of interest 272 may be the heart or another organ in the upper torso of the patient 270. Both the first and second subsets 302, 304 of transaxial contour slices 212 contain slices 212 that depict the target region of interest 272. According to an embodiment, the medical imaging system 10 provides the operator with the ability to scroll along the axial length of the patient 270 to view different versions of the subject shape outline 206 based on different subsets of the slices 212. For example, the subject shape outline 206 shown in FIG. 5 may be based on the transaxial contour slices 212 from the first subset 302 shown in FIG. 9. But, due to variations in patient shape over the length of the patient 270, a different alignment of the patient 270 relative to the gantry 20 may enable closer positioning of the detector arms 104 relative to the patient 270, and therefore better resulting image quality. For example, upon receiving a user scroll request from the operator using the user input device 39, the control circuit 32 may generate an updated version of the subject shape outline that is based on the second subset 304 of the contour slices 212. The control circuit 32 may display the updated version of the subject shape outline on the gantry visualization 204. The operator can view how the updated version of the subject shape outline compares or fits in relative to the graphical detector arms 208 displayed at the designated scan positions. For example, if the updated version of the subject shape outline has a larger area or footprint than the subject shape outline 206 shown in FIG. 5, then at least one of the graphical detector arms 208 may intersect the updated version of the subject shape outline.

In the illustrated embodiment shown in FIG. 9, the updated version of the subject shape outline based on the second subset 304 of slices 212 may have a smaller area or footprint than the subject shape outline 206 that is based on the first subset 302 of slices 212 because the first subset 302 includes slices 212 that represent an overweight gut of the patient 270. These large slices 212 enlarge the subject shape outline 206. The second subset 304 lacks the large slices 212 associated with the patient's gut, and therefore the updated subject shape outline may have a smaller area than the original subject shape outline 206. Due to the smaller area, the updated subject shape outline may enable the detector arms 104, especially the detector arms 104 located above the chest and gut of the patient 270, to move closer to the patient 270 during the imaging scan than if the original subject shape outline 206 is utilized to control the detector positioning. The closer proximity of the detector arms 104 would yield greater image quality of the target region of interest 272. In order to perform the imaging scan to achieve the benefit of greater image quality using the updated version of the subject shape outline, the operator may utilize the user input device 39 to axially reposition the patient 270 within the bore 22 such that the detector arms 104 align with the second axial segment of the patient 270 (e.g., the upper torso corresponding to the second subset 304 of the contour slices 212). Although only two subsets 302, 304 of contour slices 212 are described above, the axial scrolling functionality may enable the operator to view and select from among a multitude of different prospective axial positions of the patient 270 relative to the gantry 20. The control circuit 32 may generate and display updated versions of the subject shape outline for each axial position selected via a user scroll request.

Referring back to FIG. 5, the control circuit 32 in at least one embodiment displays a second set 350 of graphical detector arms 352 on the gantry visualization 204. The second set 350 of graphical detector arms 352 are displayed on the gantry visualization 204 to represent the current positions of the detector arms 104 of the gantry 20. Like the first set 250 of graphical detector arms 208, each of the graphical detector arms 352 in the second set 350 is associated with a different one of the detector arms 104 and is displayed on the virtual gantry visualization 204 to represent the associated detector arm 104. The control circuit 32 may obtain the current positions of the detector arms 104 relative to the gantry 20 from the detector motion controller 30 (shown in FIG. 4) and/or from position sensors on the gantry 20. For example, the detector motion controller 30 may transmit a status signal which identifies current positioning the detector arms 104 to the control circuit 32 periodically or in response to a request for current positioning data. In response to receiving updated (e.g., current) positions of the detector arms 104, the control circuit 32 may display and/or update the positions of the second set 350 of graphical detector arms 352 to reflect the current positions of the detector arms 104.

In the illustrated embodiment, the second set 350 of graphical detector arms 352 is displayed concurrently with the first set 250 of graphical detector arms 208 on the gantry visualization 204. The two sets 250, 350 are concurrently displayed such that there is a time period during which both sets 250, 350 are displayed even if there is another time period in which only one of the two sets 250, 350 is displayed. The second set 350 of graphical detector arms 352 is overlaid or superimposed on the first set 250 of graphical detector arms 208 in FIG. 5. For example, each graphical detector arm 352 in the second set 350 is superimposed on a different corresponding graphical detector arm 208 in the first set 250. The first set 250 is shown in the designated scan positions and the second set 350 is shown in the current retracted positions, so the first set 250 radially protrudes beyond the second set 350 into the bore 22 towards the subject shape outline 206. For example, the distal ends 252 of the graphical detector arms 208 in the first set 250 are radially between the subject shape outline 206 and respective distal ends 354 of the graphical detector arms 352 in the second set 350. In an embodiment, the control circuit 32 may display both the first and second sets 250, 350 during the set-up stage and optionally during the scanning stage until the detector arms 104 of the gantry 20 move to the designated scan positions. Once the current positions of the detector arms 104 match the designated scan positions, the control circuit 32 may display only one of the sets 250, 350 of graphical detector arms because there is no physical offset between the two sets 250, 350.

In one or more embodiments, the subject shape outline 206 is updated throughout the medical imaging procedure, including during the set-up stage and the scanning stage. The subject shape outline 206 is updated in real-time to reflect up-to-date positioning of the subject within the gantry 20. The operator viewing the gantry visualization 204 can see if the subject has moved and needs to be repositioned, even if the operator is in a different room than the gantry 20. The control circuit 32 may generate updated versions of the subject shape outline 206 by obtaining updated contour image data generated by reperforming the contour scan (using the contour sensors 46 shown in FIG. 4). For example, the contour scan may be performed periodically, such as every 10 seconds, every 30 seconds, every 1 minute, or the like. The control circuit 32 may control the frequency at which the contour scan is performed to generate updated contour image data for updating the subject shape outline 206. Upon the generation of each updated version of the subject shape outline 206, the control circuit 32 displays the updated version of the subject shape outline 206 on the gantry visualization 204, which allows the operator to view variations in the subject shape outline 206 over time, indicating movement of the subject or objects associated with the subject.

The first set 250 of the graphical detector arms 208 remain displayed on the gantry visualization 204 at the designated scan positions as the subject shape outline 206 is updated. The updated versions of the subject shape outline 206 allow the operator to view the updated subject-gantry geometric relationship, such as changes in the spacing between the subject shape outline 206 and the graphical detector arms 208. In an embodiment, the control circuit 32 may notify the operator if it is determined that the subject requires repositioning and/or the designated scan positions need adjustment based on the updated subject shape outline 206. For example, movement of the subject may cause the updated subject shape outline 206 to have a bulge (e.g., an enlargement) that, when displayed on the gantry visualization 204, intersects at least one of the graphical detector arms 208 of the first set 250. This intersection indicates that if the subject remains stationary at this position, at least one of the detector arms 104 will contact the subject as the detector arms 104 extend to the designated scan positions during the medical scanning stage.

The control circuit 32 is configured to notify the operator of such intersection between the subject shape outline 206 and the graphical detector arm(s) 208, to enable the operator to take remedial action to prevent the detector arms 104 from actually contacting the subject. The control circuit 32 may notify the operator of the intersection by generating an alert. The alert may be a visual alert that includes flashing lights and/or a change in the appearance of the gantry visualization 204, an audible alert that includes emitting a specific noise, an/or a vibrational alert that vibrates the user input device 39 held by the operator. For example, the control circuit 32 may modify the appearance of the gantry visualization 204 to bring the intersection to the attention of the operator by highlighting or flashing or otherwise modifying the appearance of the one or more graphical detector arms 208 that intersect the updated subject shape outline 206. Upon receiving the alert, the operator may take a remedial action that includes repositioning the subject within the gantry 20 via instruction, picking up a fallen linen, or the like, retracting the designated scan positions of the detector arms 104 associated with the graphical detector arms 208 that intersect the updated subject shape outline 206, or the like.

As described above, the medical imaging system 10 is configured to detect and alert the operator of potential or prospective contact between the subject and the detector arms 104 of the gantry 20 before the detector arms 104 are extended towards the subject to enable to the operator to take remedial action to prevent or at least reduce the likelihood of such contact during the subsequent scanning stage of the medical imaging procedure. The operator would not have access to such information by merely viewing the subject within the gantry 20, which would only provide the current positions of the subject and the detector arms 104.

During the set-up stage, the control circuit 32 may also display the target region indicator 210 on the gantry visualization 204. The target region indicator 210 represents the target region of interest of the subject which is the focus of the medical imaging procedure. The target region of interest of the subject in the illustrated embodiment may be the heart. The target region indicator 210 is displayed at an estimated location and size of the target region of interest relative to the subject shape outline 206, the gantry 20, and/or the platform 24. For example, in FIG. 5 the target region indicator 210 is displayed proximate to a top side of the platform 24, slightly left of middle of the platform 24. By displaying the target region indicator 210 during the set-up stage, the operator can view the proximity of the graphical detector arms 208 to the target region indicator 210. The operator may utilize this information to reposition the subject, such as by moving the subject axially to a different position within the bore 22, as described above, to attain a position of the subject that allows the detector arms 104 to move closer to the target region indicator 210 for the benefit of attaining improved image quality during the scanning stage.

The control circuit 32 may estimate the size and location of the target region of interest of the subject to determine the display size and location of the target region indicator 210 based on various information. For example, the control circuit 32 may overlay CT image data that shows the region of the interest (e.g., the heart in this example) on the subject shape outline 206. Based on the known location and size of the heart in the CT image data, the control circuit 32 determines the location and size of the target region indicator 210 for display on the gantry visualization. In another embodiment, the control circuit 32 may utilize a database (e.g., an atlas database) that compiles historical information about subjects other than the particular subject being imaged. Based on known characteristics of the subject, such as the orientation of the subject, the age, gender, height, weight, and the like, the control circuit 32 may look up in the database an estimated location and size of the region of interest (e.g., the heart) for displaying the target region indicator 210.

Optionally, during the set-up stage, the operator may be able to input various user-designated settings using the user input device 39 (shown in FIG. 4). For example, if the subject expresses claustrophobia, the operator may select a claustrophobic setting via the user input device 39. Upon receiving the claustrophobic setting, the control circuit 32 may adjust the designated scan positions of the detector arms 104 by retracting each of the designated scan positions by a set distance to provide more space between the subject and the detector arms 104 during the medical imaging scan. The set distance may be based on a standard or selected by the operator, such as 2 cm, 4 cm, 6 cm, or the like. For example, if the designated scan positions in the normal setting are located 1 cm from the subject shape outline 206, then upon selecting the claustrophobic setting with a set distance of 2 cm, the designated scan positions may be radially retracted 2 cm to a resulting distance of 3 cm from the subject shape outline 206. The control circuit 32 may display the first set 250 of the graphical detector arms 208 on the gantry visualization 204 at the adjusted designated scan positions to show the operator the updated subject-gantry geometric relationship. The increased distance from the subject may result in degraded image quality during the medical scanning stage, so the control circuit 32 may increase the time of the medical scanning stage and/or number of scans of the detector arms 104, relative to the normal, non-claustrophobic setting, to improve the resulting image quality.

After the set-up stage is complete, the control circuit 32 continues to display the gantry visualization 204 during the scanning stage. Although the operator may be within the same room as the gantry 20 during the set-up stage for communicating directly with the subject, the operator is typically located in a separate room from the gantry 20 during the scanning stage to avoid receiving a dose of radiation. For example, during the scanning stage the operator may view the gantry visualization 204 on the display device 40B that is located in an office of the operator. The control circuit 32 continues to update the subject shape outline 206 and to provide additional information to allow the operator to remotely monitor the progress of the scanning stage.

Figure 10:
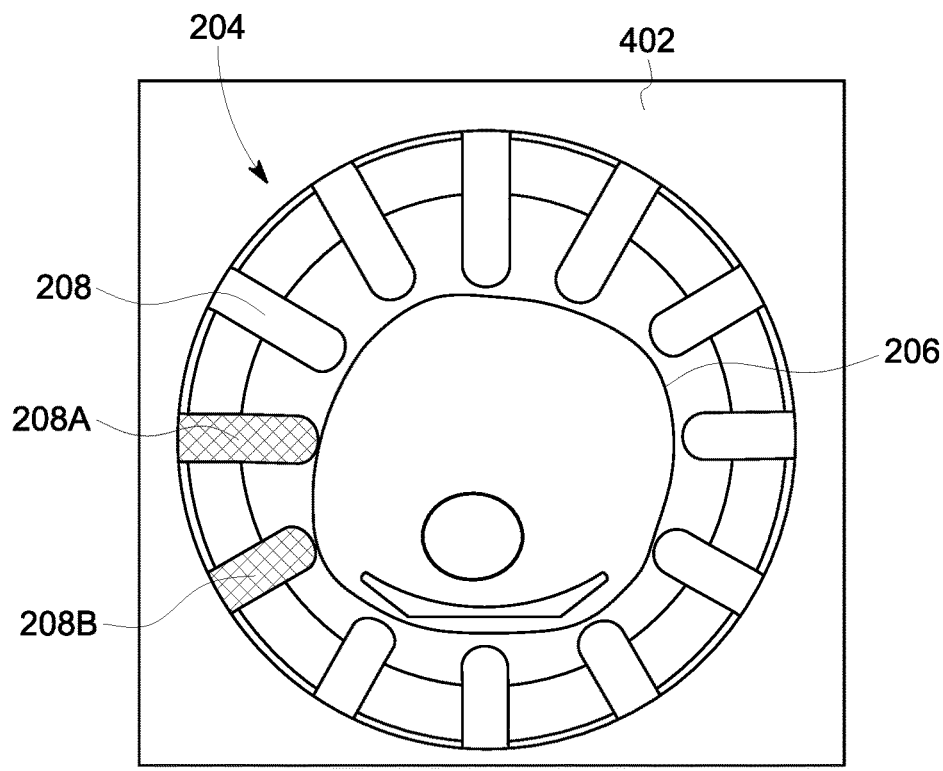
FIG. 10 illustrates the gantry visualization displayed on a display screen indicating a contact state according to an embodiment.

FIG. 10 illustrates the gantry visualization 204 displayed on a display screen 402 indicating a contact state according to an embodiment. The display screen 402 may be a screen of either of the display devices 40A, 40B shown in FIG. 4. During the scanning stage, if any of the detector arms 104 contact the subject, the control circuit 32 may notify the operator by modifying an appearance of the gantry visualization 204. The contact between the detector arms 104 and the subject may be detected by the engagement sensors 44 (shown in FIG. 4) on the detector arms 104. In an embodiment, if the control circuit 32 receives an indication of contact from the engagement sensor 44 disposed on one or more of the detector arms 104, the control circuit 32 modifies the appearance of the one or more graphical detector arms 208 on the gantry visualization 204 that correspond to the one or more detector arms 104 that experienced the contact with the subject.

In FIG. 10, the control circuit 32 highlights two of the graphical detector arms 208A, 208B based on receiving indications that the two detector arms 104 associated with the two graphical detector arms 208A, 208B engage the subject. The control circuit 32 may highlight the two graphical detector arms 208A, 208B on the gantry visualization 204 by changing a color, a shape, or a size of the graphical detector arms 208A, 208B relative to the other graphical detector arms 208, by displaying a pattern within the graphical detector arms 208A, 208B, by pulsing and/or flashing the graphical detector arms 208A, 208B or otherwise modifying the displayed appearance of the graphical detector arms 208A, 208B. In an embodiment, the contact state shown in FIG. 10 may be displayed in response to detecting contact while the detector arms 104 are stationary in fixed positions. Modifying the appearance of the graphical detector arms 208A, 208B indicates to the operator viewing the display screen 402 that the subject moved into contact with the two detector arms 104 that are associated with the two graphical detector arms 208A, 208B. The control circuit 32 may alter the subject shape outline 206 on the gantry visualization 204 to reflect the contact by extending or enlarging the area of the subject shape outline 206 proximate to the graphical detector arms 208A, 208B. The control circuit 32 may also generate another type of alert in addition to modifying the appearance of the graphical detector arms 208A, 208B, such as emitting an audible alert, generating a visual alert by flashing lights, and/or generating a vibrational alert by vibrating the user input device 39 held by the operator. Upon being notified of the movement by the subject that caused the contact, the operator may use the user input device 39 to pause the medical imaging scan, to instruct the subject to move out of contact with the detector arms 104, to modify the designated scan positions of the engaging detector arms 104, and/or the like.

Figure 11:
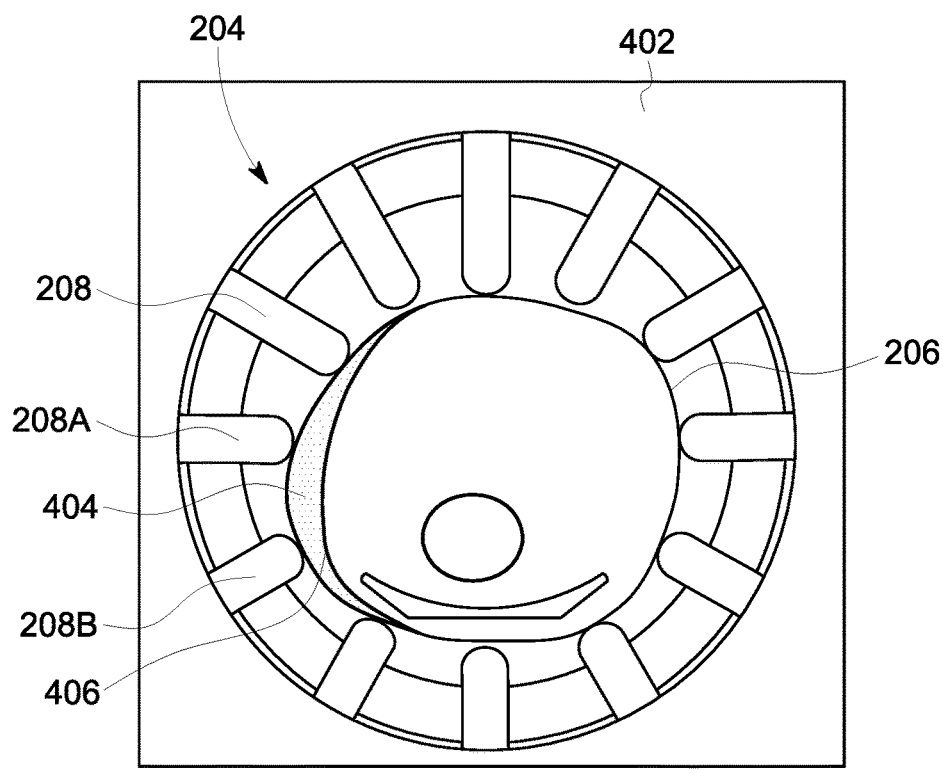
FIG. 11 illustrates the gantry visualization displayed on the display screen indicating another contact state according to an embodiment.

FIG. 11 illustrates the gantry visualization 204 displayed on the display screen 402 indicating another contact state according to an embodiment. The gantry 20 may be configured such that if any of the detector arms 104 engage the subject with a force greater than a designated threshold amount of force and/or while the detector arms 104 are moving from retracted positions towards the designated scan positions, the detector arms 104 that contacted the subject are automatically retracted a distance sufficient to alleviate the contact with the subject. In FIG. 11, the two graphical detector arms 208A, 208B are shown in retracted positions because the subset of detector arms 104 associated with the graphical detector arms 208A, 208B were automatically retracted due to contact with the subject. The contact may have been initiated by the detector arms 104 as the detector arms 104 moved towards the designated scan positions at the beginning of the scanning stage. Alternatively, the contact may have been initiated by the subject and the force involved may have been greater than the designated threshold amount of force, as measured by the respective engagement sensors 44.

In the illustrated embodiment, the control circuit 32 modifies the appearance of the two graphical detector arms 208A, 208B on the gantry visualization 204 to reflect the retraction of the associated detector arms 104. For example, the detector motion controller 30 (shown in FIG. 4) may communicate to the control circuit 32 the current, retracted positions of the two detector arms 104. As shown in FIG. 11, the two graphical detector arms 208A, 208B do not extend as far radially into the bore 22 as the same two graphical detector arms 208A, 208B do in FIG. 10. Furthermore, the control circuit 32 may modify the appearance of the subject shape outline 206 to reflect the position of the subject during the contact based on the retraction distances of the detector arms 104. For example, the control circuit 32 shows a protuberance area 404 between the pre-existing subject shape outline 206 and the graphical detector arms 208A, 208B that are modified to reflect the retraction. The protuberance area 404 may be differentiated from the pre-existing subject shape outline 206 via being displayed in a different color, pattern, intensity, or the like, and/or by displaying a line 406 showing the perimeter of the pre-existing subject shape outline 206 from which the protuberance area 404 extends.

Although the examples above describe movement by the subject that causes contact with the detector arms 104, it is recognized that object on or associated with the subject may also cause contact with the detector arms 104 which is displayed on the gantry visualization 204 to notify the operator. For example, contact may be caused by a linen or another object falling from the subject into contact with one or more of the detector arms 104.

Figure 12:
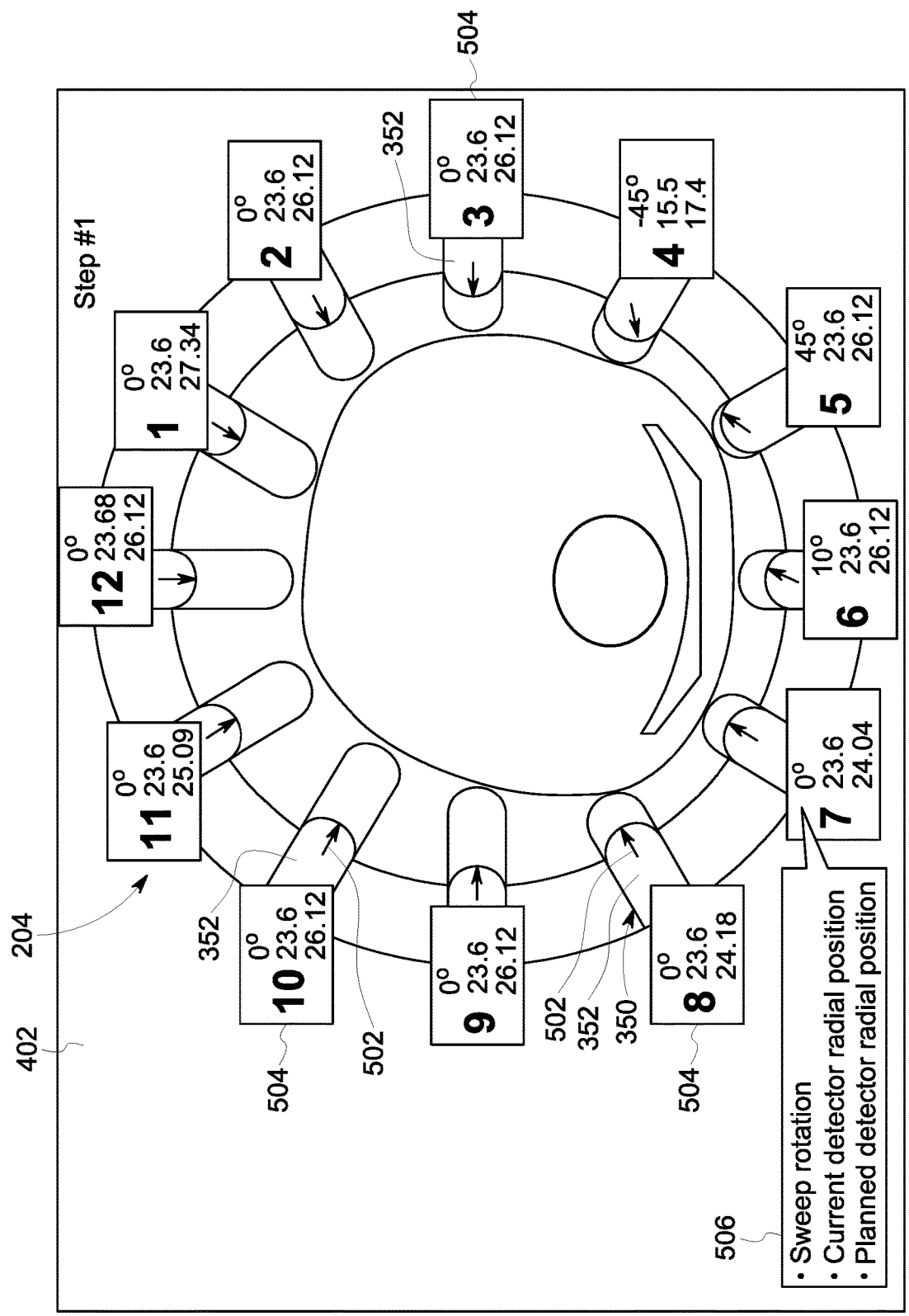
FIG. 12 illustrates the gantry visualization displayed on the display screen showing an additional information state according to an embodiment.

FIG. 12 illustrates the gantry visualization 204 displayed on the display screen 402 showing an additional information state according to an embodiment. In addition to displaying the subject-gantry geometric relationship, the control circuit 32 may display additional information on the gantry visualization 204 for the operator. The additional information may be provided for various purposes, such as for debugging, analyzing, and/or troubleshooting the medical imaging system 10. As an example of the additional information that may be provided, the control circuit 32 may display a sweep direction indicator 502 on each of the graphical detector arms 352 in the second set 350. The sweep direction indicator 502 may be an arrow that indicates the current sweep rotation position of each corresponding detector arm 104.

Optionally, the control circuit 32 may display information boxes 504 on the display screen 402 that are adjacent to the different graphical detector arms 352. Each of the information boxes 504 display operating parameters of the specific detector arm 104 associated with the graphical detector arm 352 that is adjacent to the information box 504. For example, the information box 504 labeled with a "3" is adjacent to a third graphical detector arm 352 and displays operating parameters of the detector arm 104 that is associated with the third graphical detector arm 352. In the illustrated embodiment, the operating parameters displayed in the information boxes 504 include the sweep rotation position (e.g., in degrees), the current detector radial extension position, and the planned detector radial extension position (e.g., the designated scan position), as indicated by the key 506. The information boxes 504 and/or sweep position indicators 502 may be automatically displayed on the gantry visualization 204 or may be displayed upon request in response to the operator selecting a setting to display such additional information.

Figure 13:
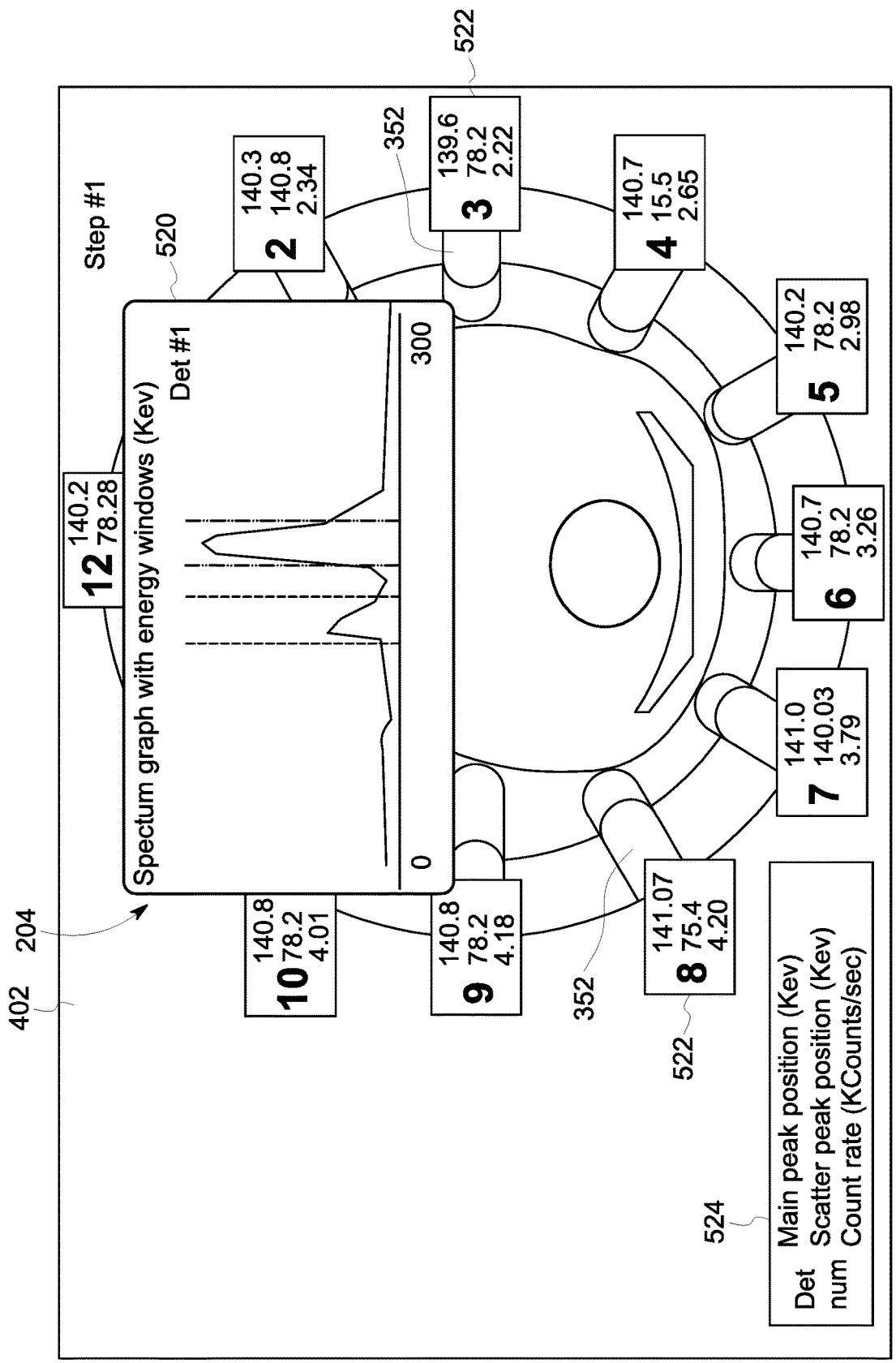
FIG. 13 illustrates the gantry visualization displayed on the display screen showing a diagnostic state according to an embodiment.

FIG. 13 illustrates the gantry visualization 204 displayed on the display screen 402 showing a diagnostic state according to an embodiment. The gantry visualization 204 in the diagnostic state displays diagnostic-related data and parameters of the detector arms 104. For example, when in the diagnostic state, upon receive of a user input selecting one of the graphical detector arms 352, the control circuit 32 displays an energy histogram 520 on the display screen 402. The energy histogram 520 is associated with the detector arm 104 that is associated with the graphical detector arm 352 selected by the operator. The operator may select the graphical detector arm 352 using the user input device 39 to scroll a cursor over the graphical detector arm 352 and/or to press a selection button while the cursor is over the graphical detector arm 352. The energy histogram 520 displays information about the detector arm 104 functionality, and may be useful during maintenance of the medical imaging system 10 and/or the medical imaging apparatus 12 thereof. In addition to providing energy histograms 520, the gantry visualization 204 in the diagnostic state may also provide additional information within information boxes 522, such as main peak position, scatter peak position, and count rate, as indicated by the key 524.

Figure 14:
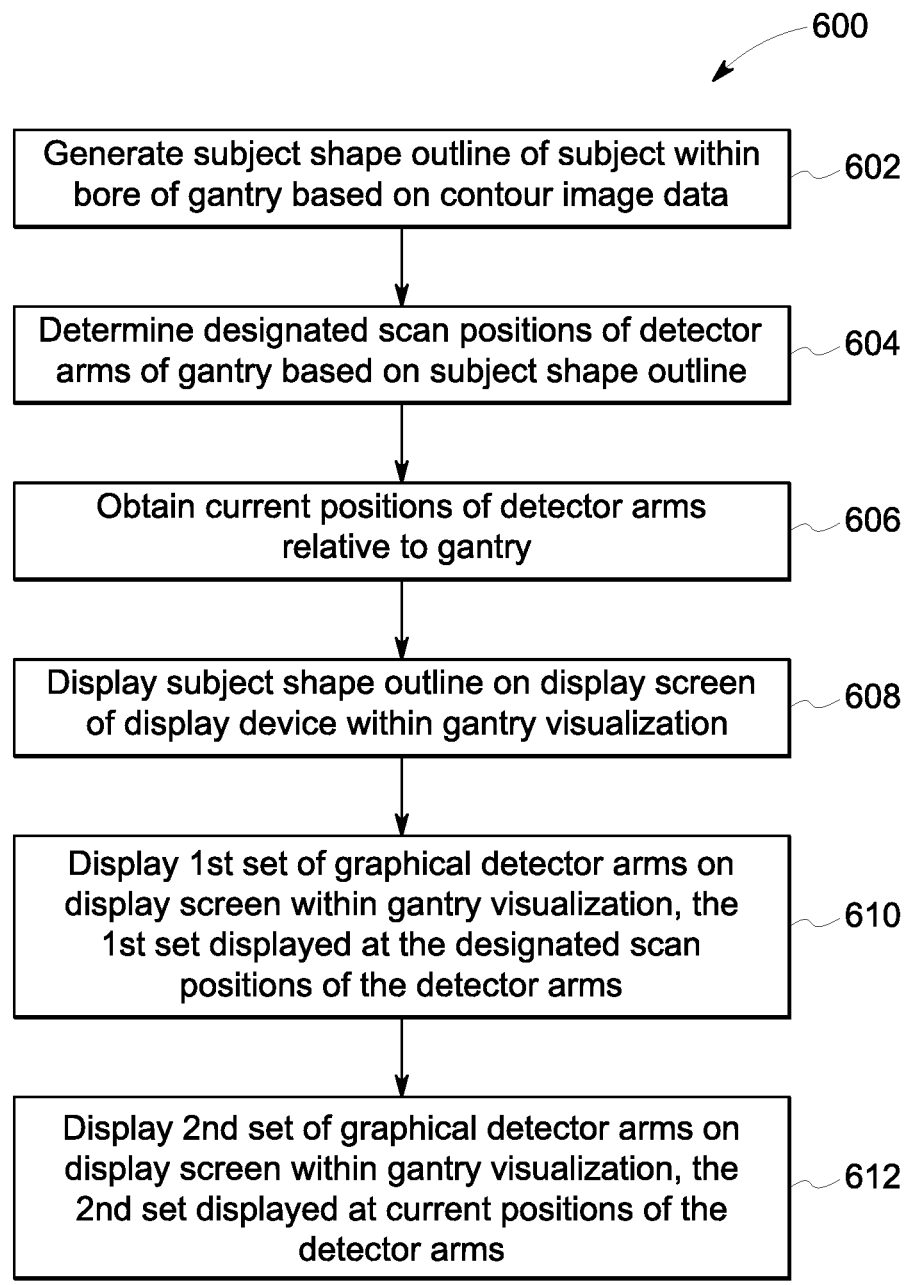
FIG. 14 is a flowchart of a method for providing automated assistance during a medical imaging procedure according to an embodiment.

FIG. 14 is a flowchart of a method 600 for providing automated assistance during a medical imaging procedure according to an embodiment. The method 600 may represent at least some of the operations performed by the control circuit 32, including the one or more processors thereof, of the medical imaging system 10 shown in FIG. 2. The method 600 may represent an algorithm used to create (e.g., write) one or more software applications that direct operation of one or more processors of the control circuit 32. The method 600 may include additional steps, fewer steps, and/or different steps in an alternative embodiment than are shown in the illustrated flowchart. Furthermore, the entire method 600, or portions thereof, may repeat multiple times during the medical imaging procedure.

Referring to FIGS. 1 through 13, the method 600 begins at 602, at which a subject shape outline 206 of a subject that is disposed at least partially within a bore 22 of a gantry 20 of a medical imaging apparatus 12 is generated. The subject shape outline 206 is generated based on contour image data of the subject. The gantry 20 includes at least three detector arms 104 circumferentially spaced apart along a perimeter of the bore 22. The detector arms 104 are radially movable relative to the gantry 20 towards and away from the subject.

At 604, designated scan positions for the detector arms 104 are determined based on the subject shape outline 206. For example, the designated scan positions are determined as positions in which the detector arms 104 are within a designated threshold proximity of the subject shape outline 206 without intersecting the subject shape outline 206. The detectors arms 104 are moved to the designated scan positions from retracted positions prior to starting a scanning stage. During the scanning stage, the detector arms 104 generate medical image data of an internal region of the subject.

At 606, current positions of the detector arms 104 relative to the gantry 20 are obtained. The current positions may be obtained by a detector motion controller 30 that controls the positioning and movement of the detector arms 104. The current positions of the detector arms 104 may be retracted or extended depending on whether the medical imaging procedure is in a set-up stage or the scanning stage.

At 608, the subject shape outline 206 is displayed on a display screen 202 of a display device 40 within a gantry visualization 204. The gantry visualization 204 is a graphical representation of the gantry 20 showing the bore 22. The subject shape outline 206 is displayed within the bore 22 of the gantry visualization 204. At 610, a first set 250 of graphical detector arms 208 are displayed on the display screen 202 within the gantry visualization 204. The graphical detector arms 208 are displayed concurrently with the subject shape outline 206. Each of the graphical detector arms 208 in the first set 250 is associated with a different one of the detector arms 104 of the gantry 20. The graphical detector arms 208 in the first set 250 are displayed at the designated scan positions relative to the gantry 20 of the gantry visualization 204.

At 612, a second set 350 of graphical detector arms 352 are displayed on the display screen 202 within the gantry visualization 204. The graphical detector arms 352 in the second set 350 are displayed at the current positions of the detector arms 104 relative to the gantry 20 of the gantry visualization 204. The second set 350 may be superimposed on the first set 250. Displaying the graphical detector arms 208, 352 and the subject shape outline 206 together on the gantry visualization 204 shows a subject-gantry geometric relationship. The gantry visualization 204 provides the operator with information about the subject-gantry geometric relationship that may not have previously been attainable by an operator via conventional imaging and monitoring tactics. The gantry visualization 204 can be used by the operator during set-up and scanning stages of the medical imaging procedure, as well as for diagnostics, troubleshooting, and maintenance.

It is noted that the operations described in steps 606, 608, 610, and 612 may repeat for every rotation step within a given image acquisition. For example, after step 612, the gantry 20 may rotate the detector arms 104 to a different rotational position relative to the subject, and the method 600 may return to 606 to obtain updated current positions of the detector arms 104 relative to the gantry 20. The method 600 may proceed from step 606 through step 612 at each of the different rotation steps.

In one or more embodiments, a medical imaging system is provided that includes a gantry, a display device, and a control circuit. The gantry defines a bore configured to receive a subject therein. The gantry includes at least three detector arms circumferentially spaced apart along a perimeter of the bore and radially movable relative to the gantry towards and away from the subject. The display device includes a display screen. The control circuit includes one or more processors communicatively connected to the display device. The control circuit is configured to generate a subject shape outline of the subject disposed at least partially within the bore based on obtained contour image data of the subject. The control circuit is configured to determine designated scan positions of the detector arms based on the subject shape outline. Respective distal ends of the detector arms at the designated scan positions are within a designated threshold proximity of the subject shape outline without intersecting the subject shape outline. The control circuit is configured to display the subject shape outline on the display screen of the display device within a gantry visualization that is a graphical representation of the gantry showing the bore. The subject shape outline is displayed within the bore of the gantry visualization. The control circuit is configured to display a first set of graphical detector arms on the display screen within the gantry visualization. Each of the graphical detector arms in the first set is associated with a different one of the detector arms of the gantry. The graphical detector arms are displayed at the designated scan positions relative to the gantry of the gantry visualization to show a subject-gantry geometric relationship.

Optionally, the gantry has at least eight detector arms circumferentially spaced along the perimeter of the bore.

Optionally, the detector arms include detection heads at the distal ends thereof. The detection heads are configured to monitor radiation emitted from the subject for generating nuclear medicine image data depicting one or more internal elements of the subject.

Optionally, the gantry is a component of a nuclear medicine imaging apparatus and the display device is disposed in a separate room from the gantry to allow an operator to view the subject-gantry geometric relationship via the gantry visualization on the display screen during a nuclear imaging scan of the subject without exposing the operator to a dose of radiation.

Optionally, the gantry further includes a detector motion controller that controls radial positioning of the detector arms. The control circuit is configured to obtain current positions of the detector arms relative to the gantry from the detector motion controller and to display a second set of graphical detector arms on the display screen within the gantry visualization. The graphical detector arms in the second set are displayed at the current positions relative to the gantry of the gantry visualization. Optionally, each of the graphical detector arms in the second set is superimposed on a corresponding graphical detector arm in the first set that represents the same detector arm of the gantry.

Optionally, the control circuit is further configured to estimate a location of a target region of interest of the subject, and to display a target region indicator representing the target region of interest on the display screen within the subject shape outline.

Optionally, the medical imaging system also includes engagement sensors mounted at the distal ends of the detector arms and communicatively connected to the control circuit. Responsive to detecting contact between the subject and at least one of the detector arms via the engagement sensors, the control circuit is configured to generate at least one of an audible alert, a visual alert, or a vibrational alert to notify an operator.

Optionally, the medical imaging system also includes engagement sensors mounted at the distal ends of the detector arms and communicatively connected to the control circuit. Responsive to detecting contact between the subject and at least one of the detector arms via the engagement sensors while the detector arms are stationary, the control circuit is configured to modify an appearance of at least one of the graphical detector arms on the gantry visualization corresponding to the at least one of the detector arms that experienced the contact with the subject.

Optionally, the control circuit generates the subject shape outline based on a first subset of transaxial contour slices that depicts a first axial segment of the subject. The transaxial contour slices represent the contour image data. Responsive to receiving a user scroll request, the control circuit is configured to generate an updated version of the subject shape outline based on a second subset of the transaxial contour slices that depicts a second axial segment of the subject. The control circuit displays the updated version of the subject shape outline on the gantry visualization.

In one or more embodiments, a method (e.g., for automated medical imaging assistance) is provided that includes generating a subject shape outline of a subject disposed at least partially within a bore of a gantry of a medical imaging apparatus based on contour image data of the subject. The gantry includes at least three detector arms circumferentially spaced apart along a perimeter of the bore of the gantry. The detector arms are radially movable relative to the gantry towards and away from the subject. The method includes determining designated scan positions of the detector arms based on the subject shape outline. Respective distal ends of the detector arms at the designated scan positions are within a designated threshold proximity of the subject shape outline without intersecting the subject shape outline. The method includes displaying the subject shape outline on a display screen of a display device within a gantry visualization that is a graphical representation of the gantry showing the bore. The subject shape outline is displayed within the bore of the gantry visualization. The method also includes displaying a first set of graphical detector arms on the display screen within the gantry visualization. Each of the graphical detector arms in the first set is associated with a different one of the detector arms of the gantry, and the graphical detector arms are displayed at the designated scan positions relative to the gantry of the gantry visualization to show a subject-gantry geometric relationship.

Optionally, the method also includes obtaining current positions of the detector arms relative to the gantry from a detector motion controller of the medical imaging apparatus, and displaying a second set of graphical detector arms within the gantry visualization on the display screen. The graphical detector arms in the second set are displayed at the current positions relative to the gantry of the gantry visualization.

Optionally, the method also includes periodically generating an updated version of the subject shape outline based on updated contour image data of the subject. The displaying of the subject shape outline on the gantry visualization includes displaying the updated version of the subject shape outline upon receipt thereof to reflect up-to-date positioning of the subject.

Optionally, the method also includes displaying a sweep direction indicator on each of the graphical detector arms of the gantry visualization.

Optionally, the method also includes displaying information boxes on the display screen adjacent to the different graphical detector arms on the gantry visualization. Each of the information boxes displays operating parameters of the specific detector arm associated with the graphical detector arm that is adjacent to the information box.

Optionally, the method also includes estimating a location of a target region of interest of the subject, and displaying a target region indicator that represents the target region of interest on the display screen within the subject shape outline.

Optionally, the method also includes, responsive to receiving a user input selecting one of the graphical detector arms, displaying an energy histogram on the display screen. The energy histogram is associated with the detector arm that corresponds to the graphical detector arm that is selected.

Optionally, the method also includes, responsive to detecting contact between the subject and at least one of the detector arms while the detector arms are stationary, modifying an appearance of at least one of the graphical detector arms on the gantry visualization corresponding to the at least one of the detector arms that experienced the contact with the subject.

Optionally, the method also includes, responsive to detecting contact between the subject and a subset of the detector arms while the detector arms are radially moving towards the designated scan positions, radially retracting the subset of the detector arms that contacted the subject a distance sufficient to alleviate the contact with the subject. The method also includes modifying an appearance of the graphical detector arms that correspond to the subset of the detector arms to reflect the retraction of the subset, and modifying an appearance of the subject shape outline on the gantry visualization to include a protuberance area between the subject shape outline and the graphical detector arms that are modified to reflect the retraction.

In one or more embodiments, a medical imaging system is provided that includes a gantry, a display device, and a control circuit. The gantry defines a bore configured to receive a subject therein. The gantry includes multiple detector arms circumferentially spaced apart along a perimeter of the bore and radially movable relative to the gantry towards and away from the subject. The display device includes a display screen. The control circuit includes one or more processors communicatively connected to the display device. The control circuit is configured to generate a subject shape outline of the subject disposed at least partially within the bore based on obtained contour image data of the subject. The control circuit is configured to display the subject shape outline on the display screen within a gantry visualization that is a graphical representation of the gantry showing the bore. The subject shape outline is displayed within the bore of the gantry visualization. The control circuit is configured to determine designated scan positions of the detector arms based on the subject shape outline such that respective distal ends of the detector arms at the designated scan positions are within a designated threshold proximity of the subject shape outline without intersecting the subject shape outline. The control circuit is configured to display a first set of graphical detector arms on the display screen within the gantry visualization. Each of the graphical detector arms is associated with a different one of the detector arms of the gantry. The graphical detector arms in the first set are displayed at the respective designated scan positions relative to the gantry of the gantry visualization. The control circuit is also configured to determine current positions of the detector arms relative to the gantry, and to display a second set of graphical detector arms on the display screen within the gantry visualization. The graphical detector arms in the second set are displayed at the respective current positions of the detector arms relative to the gantry of the gantry visualization. Each of the graphical detector arms in the second set is superimposed on a corresponding graphical detector arm in the first set that represents the same detector arm of the gantry.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are example embodiments. Many other embodiments will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A medical imaging system comprising:
a gantry defining a bore configured to receive a subject therein, the gantry including at least three detector arms circumferentially spaced apart along a perimeter of the bore and radially movable relative to the gantry towards and away from the subject;
a display device including a display screen; and
a control circuit including one or more processors communicatively connected to the display device, the control circuit configured to generate a subject shape outline of the subject disposed at least partially within the bore based on obtained contour image data of the subject, the control circuit configured to determine designated scan positions of the detector arms based on the subject shape outline, wherein respective distal ends of the detector arms at the designated scan positions are within a designated threshold proximity of the subject shape outline without intersecting the subject shape outline,
wherein the control circuit is configured to display the subject shape outline on the display screen of the display device within a gantry visualization that is a graphical representation of the gantry showing the bore, the subject shape outline displayed within the bore of the gantry visualization, and
wherein the control circuit is configured to display a first set of graphical detector arms on the display screen within the gantry visualization, each of the graphical detector arms in the first set associated with a different one of the detector arms of the gantry, the graphical detector arms displayed at the designated scan positions relative to the gantry of the gantry visualization to show a subject-gantry geometric relationship.

2. The medical imaging system of claim 1, wherein the gantry has at least eight detector arms circumferentially spaced along the perimeter of the bore.

3. The medical imaging system of claim 1, wherein the detector arms include detection heads at the distal ends thereof, the detection heads configured to monitor radiation emitted from the subject for generating nuclear medicine image data depicting one or more internal elements of the subject.

4. The medical imaging system of claim 1, wherein the gantry is a component of a nuclear medicine imaging apparatus and the display device is disposed in a separate room from the gantry to allow an operator to view the subject-gantry geometric relationship via the gantry visualization on the display screen during a nuclear imaging scan of the subject without exposing the operator to a dose of radiation.

5. The medical imaging system of claim 1, wherein the gantry further includes a detector motion controller that controls radial positioning of the detector arms, wherein the control circuit is configured to obtain current positions of the detector arms relative to the gantry from the detector motion controller and to display a second set of graphical detector arms on the display screen within the gantry visualization, wherein the graphical detector arms in the second set are displayed at the current positions relative to the gantry of the gantry visualization.

6. The medical imaging system of claim 5, wherein each of the graphical detector arms in the second set is superimposed on a corresponding graphical detector arm in the first set that represents the same detector arm of the gantry.

7. The medical imaging system of claim 1, wherein the control circuit is further configured to estimate a location of a target region of interest of the subject, and to display a target region indicator representing the target region of interest on the display screen within the subject shape outline.

8. The medical imaging system of claim 1, further comprising engagement sensors mounted at the distal ends of the detector arms and communicatively connected to the control circuit, wherein, responsive to detecting contact between the subject and at least one of the detector arms via the engagement sensors, the control circuit is configured to generate at least one of an audible alert, a visual alert, or a vibrational alert to notify an operator.

9. The medical imaging system of claim 1, further comprising engagement sensors mounted at the distal ends of the detector arms and communicatively connected to the control circuit, wherein, responsive to detecting contact between the subject and at least one of the detector arms via the engagement sensors while the detector arms are stationary, the control circuit is configured to modify an appearance of at least one of the graphical detector arms on the gantry visualization corresponding to the at least one of the detector arms that experienced the contact with the subject.

10. The medical imaging system of claim 1, wherein the control circuit generates the subject shape outline based on a first subset of transaxial contour slices that depicts a first axial segment of the subject, the transaxial contour slices representing the contour image data, and wherein, responsive to receiving a user scroll request, the control circuit is configured to generate an updated version of the subject shape outline based on a second subset of the transaxial contour slices that depicts a second axial segment of the subject, and the control circuit displays the updated version of the subject shape outline on the gantry visualization.

11. A method comprising:
generating a subject shape outline of a subject disposed at least partially within a bore of a gantry of a medical imaging apparatus based on contour image data of the subject, the gantry including at least three detector arms circumferentially spaced apart along a perimeter of the bore of the gantry, the detector arms radially movable relative to the gantry towards and away from the subject;
determining designated scan positions of the detector arms based on the subject shape outline, wherein respective distal ends of the detector arms at the designated scan positions are within a designated threshold proximity of the subject shape outline without intersecting the subject shape outline;
displaying the subject shape outline on a display screen of a display device within a gantry visualization that is a graphical representation of the gantry showing the bore, the subject shape outline displayed within the bore of the gantry visualization; and
displaying a first set of graphical detector arms on the display screen within the gantry visualization, wherein each of the graphical detector arms in the first set is associated with a different one of the detector arms of the gantry, and the graphical detector arms are displayed at the designated scan positions relative to the gantry of the gantry visualization to show a subject-gantry geometric relationship.

12. The method of claim 11, further comprising obtaining current positions of the detector arms relative to the gantry from a detector motion controller of the medical imaging apparatus, and displaying a second set of graphical detector arms within the gantry visualization on the display screen, wherein the graphical detector arms in the second set are displayed at the current positions relative to the gantry of the gantry visualization.

13. The method of claim 11, further comprising periodically generating an updated version of the subject shape outline based on updated contour image data of the subject, wherein the displaying of the subject shape outline on the gantry visualization includes displaying the updated version of the subject shape outline upon receipt thereof to reflect up-to-date positioning of the subject.

14. The method of claim 11, further comprising displaying a sweep direction indicator on each of the graphical detector arms of the gantry visualization.

15. The method of claim 11, further comprising displaying information boxes on the display screen adjacent to the different graphical detector arms on the gantry visualization, each of the information boxes displaying operating parameters of the specific detector arm associated with the graphical detector arm that is adjacent to the information box.

16. The method of claim 11, further comprising estimating a location of a target region of interest of the subject, and displaying a target region indicator that represents the target region of interest on the display screen within the subject shape outline.

17. The method of claim 11, further comprising, responsive to receiving a user input selecting one of the graphical detector arms, displaying an energy histogram on the display screen, the energy histogram associated with the detector arm that corresponds to the graphical detector arm that is selected.

18. The method of claim 11, further comprising, responsive to detecting contact between the subject and at least one of the detector arms while the detector arms are stationary, modifying an appearance of at least one of the graphical detector arms on the gantry visualization corresponding to the at least one of the detector arms that experienced the contact with the subject.

19. The method of claim 11, further comprising, responsive to detecting contact between the subject and a subset of the detector arms while the detector arms are radially moving towards the designated scan positions, radially retracting the subset of the detector arms that contacted the subject a distance sufficient to alleviate the contact with the subject, modifying an appearance of the graphical detector arms that correspond to the subset of the detector arms to reflect the retraction of the subset, and modifying an appearance of the subject shape outline on the gantry visualization to include a protuberance area between the subject shape outline and the graphical detector arms that are modified to reflect the retraction.

20. A medical imaging system comprising:
a gantry defining a bore configured to receive a subject therein, the gantry including multiple detector arms circumferentially spaced apart along a perimeter of the bore and radially movable relative to the gantry towards and away from the subject;
a display device including a display screen; and
a control circuit including one or more processors communicatively connected to the display device, the control circuit configured to generate a subject shape outline of the subject disposed at least partially within the bore based on obtained contour image data of the subject, the control circuit configured to display the subject shape outline on the display screen within a gantry visualization that is a graphical representation of the gantry showing the bore, the subject shape outline displayed within the bore of the gantry visualization, the control circuit configured to determine designated scan positions of the detector arms based on the subject shape outline such that respective distal ends of the detector arms at the designated scan positions are within a designated threshold proximity of the subject shape outline without intersecting the subject shape outline, the control circuit configured to display a first set of graphical detector arms on the display screen within the gantry visualization, each of the graphical detector arms associated with a different one of the detector arms of the gantry, the graphical detector arms in the first set displayed at the respective designated scan positions relative to the gantry of the gantry visualization,
wherein the control circuit is also configured to determine current positions of the detector arms relative to the gantry, and to display a second set of graphical detector arms on the display screen within the gantry visualization, the graphical detector arms in the second set displayed at the respective current positions of the detector arms relative to the gantry of the gantry visualization, wherein each of the graphical detector arms in the second set is superimposed on a corresponding graphical detector arm in the first set that represents the same detector arm of the gantry.

* * * * *